(12) United States Patent
Kaku et al.

(10) Patent No.: US 12,059,976 B2
(45) Date of Patent: Aug. 13, 2024

(54) IN-SEAT EXPERIENCE SYSTEM

(71) Applicant: TS TECH CO., LTD., Asaka (JP)

(72) Inventors: Hiroyuki Kaku, Tochigi (JP); Satoru Kaneda, Tochigi (JP); Munetaka Kowa, Tochigi (JP); Hiroyuki Numajiri, Tochigi (JP); Satoshi Fujita, Tochigi (JP); Takako Miyoshi, Tochigi (JP); Atsushi Kusano, Tochigi (JP); Ryuichiro Hirose, Tochigi (JP); Yoshikazu Ito, Tochigi (JP); Yousuke Higashi, Tochigi (JP); Satoshi Suzuki, Tochigi (JP); Ryosuke Sato, Tochigi (JP); Kento Uetake, Tochigi (JP)

(73) Assignee: TS TECH CO., LTD., Saitama (JP)

( * ) Notice: Subject to any disclaimer, the term of this patent is extended or adjusted under 35 U.S.C. 154(b) by 876 days.

(21) Appl. No.: 16/972,265

(22) PCT Filed: Jun. 4, 2019

(86) PCT No.: PCT/JP2019/022127
§ 371 (c)(1),
(2) Date: Dec. 4, 2020

(87) PCT Pub. No.: WO2019/235462
PCT Pub. Date: Dec. 12, 2019

(65) Prior Publication Data
US 2021/0237617 A1 Aug. 5, 2021

(30) Foreign Application Priority Data

Jun. 7, 2018 (JP) .................................. 2018-109648
Jun. 22, 2018 (JP) .................................. 2018-118418

(51) Int. Cl.
*B60N 2/00* (2006.01)
*A63F 9/24* (2006.01)
(Continued)

(52) U.S. Cl.
CPC ................ *B60N 2/002* (2013.01); *G01L 9/02* (2013.01); *G01S 19/01* (2013.01);
(Continued)

(58) Field of Classification Search
None
See application file for complete search history.

(56) References Cited

U.S. PATENT DOCUMENTS 6,348,663 B1  2/2002 Schoos et al.
6,392,550 B1  5/2002 Najor
(Continued)

FOREIGN PATENT DOCUMENTS

DE  102006016716  10/2007
DE  102009036278  2/2011
(Continued)

OTHER PUBLICATIONS

Machine translation of DE-102016010406-A1 (Year: 2018).*
(Continued)

*Primary Examiner* — Peter J Iannuzzi
(74) *Attorney, Agent, or Firm* — HSML P.C.

(57) ABSTRACT

An in-seat experience system includes: a seat which includes a seat body, a sensor, and a seat controller allowed to acquire a measurement value from the sensor; an experience instruction device connected to the seat controller, configured to notify an occupant seated on the seat body a motion instruction and to store user identification information; and a server capable of communicating with the experience instruction device. The experience instruction device makes a determination based upon a measurement value of the sensor as to whether or not a first condition is satisfied, and to transmit a result of the determination to the server when at least the first condition is satisfied, and the server is allowed to increase a point score stored for the corresponding user
(Continued)

identification information with a condition that the result of the determination that the first condition is satisfied is received from the experience instruction device.

6 Claims, 18 Drawing Sheets

(51) Int. Cl.
  *G01L 9/02* (2006.01)
  *G01S 19/01* (2010.01)
  *G05B 19/4155* (2006.01)

(52) U.S. Cl.
  CPC .. *G05B 19/4155* (2013.01); *A63F 2009/2447* (2013.01); *G05B 2219/40175* (2013.01)

(56) References Cited

U.S. PATENT DOCUMENTS

| | | | |
|---|---|---|---|
| 7,821,382 | B2 | 10/2010 | Kameyama |
| 9,795,322 | B1 | 10/2017 | Karunaratne et al. |
| 2001/0040056 | A1 | 11/2001 | Schoos et al. |
| 2004/0133082 | A1 | 7/2004 | Abraham-Fuchs et al. |
| 2009/0030619 | A1 | 1/2009 | Kameyama |
| 2017/0251979 | A1 | 9/2017 | Franz et al. |
| 2018/0304774 | A1 | 10/2018 | Mizoi |

FOREIGN PATENT DOCUMENTS

| | | |
|---|---|---|
| DE | 102016010406 A1 * | 3/2018 |
| JP | H11-64131 | 3/1999 |
| JP | 2000314667 | 11/2000 |
| JP | 2001502986 | 3/2001 |
| JP | 2007233731 | 9/2007 |
| JP | 2009023613 | 2/2009 |
| JP | 2015108854 | 6/2015 |
| JP | 2015192800 | 11/2015 |
| JP | 2015194798 | 11/2015 |
| JP | 2017081194 | 5/2017 |
| JP | 2017176643 | 10/2017 |
| JP | 2018020738 | 2/2018 |

OTHER PUBLICATIONS

First Examination Report issued for Indian Patent Application No. 202147000028, dated Dec. 28, 2021, 5 pages.
International Search Report and Written Opinion issued for International Patent Application No. PCT/JP2019/022127, Date of mailing: Aug. 20, 2019, 16 pages including English translation.
Rejection Decision issued for Chinese Patent Application No. 201980038828.7, dated May 27, 2023, 11 pages including English translation.
Notification of Reason(s) for Refusal issued for Japanese Patent Application No. 2022-127540, Dispatch Date: Aug. 16, 2023, 5 pages including English translation.
Extended European Search Report issued for European Patent Application No. 19815571.5, dated Jul. 5, 2021, 8 pages.
Office Action issued for Japanese Patent Application No. 2020-523112, Dispatch Date: Aug. 17, 2021, 4 pages Including English translation.
Second Office Action issued for Chinese Patent Application No. 201980038828.7, dated Jan. 11, 2023, 17 pages including English translation.
Communication pursuant to Article 94(3) EPC issued for European Patent Application No. 19815571.5, dated Mar. 15, 2023, 5 pages.
Decision of Refusal issued for Japanese Patent Application No. 2020-523112, Dispatch Date: May 17, 2022, 5 pages including English translation.
First Office Action issued for Chinese Patent Application No. 201980038828.7, dated May 25, 2022, 13 pages including English translation.
Hearing Notice issued for Indian Patent Application No. 202147000028, Date of Dispatch: Jan. 9, 2024, 3 pages.

* cited by examiner

FIG.14
(a)
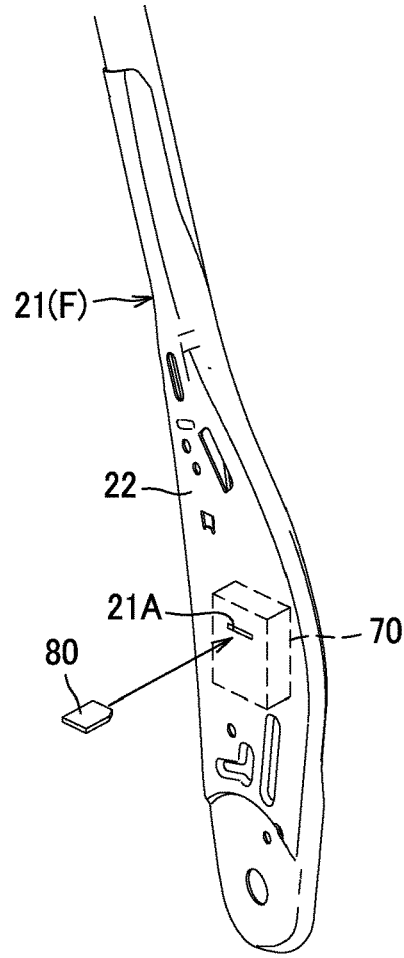
(b)
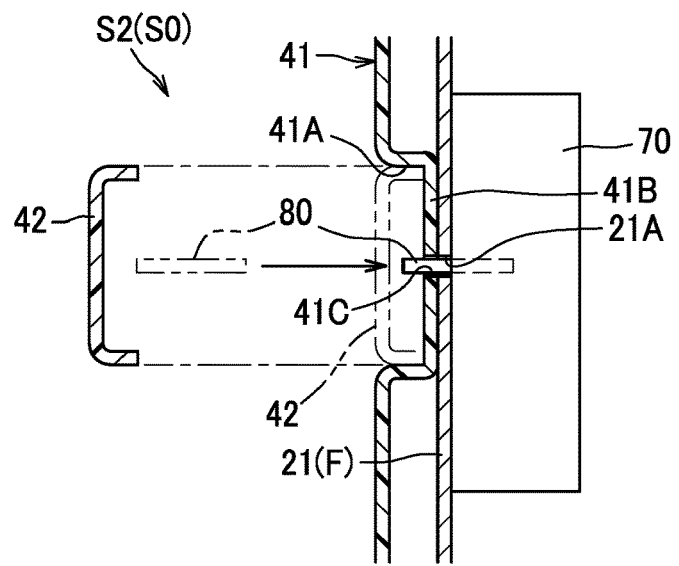

FIG.16
(a)
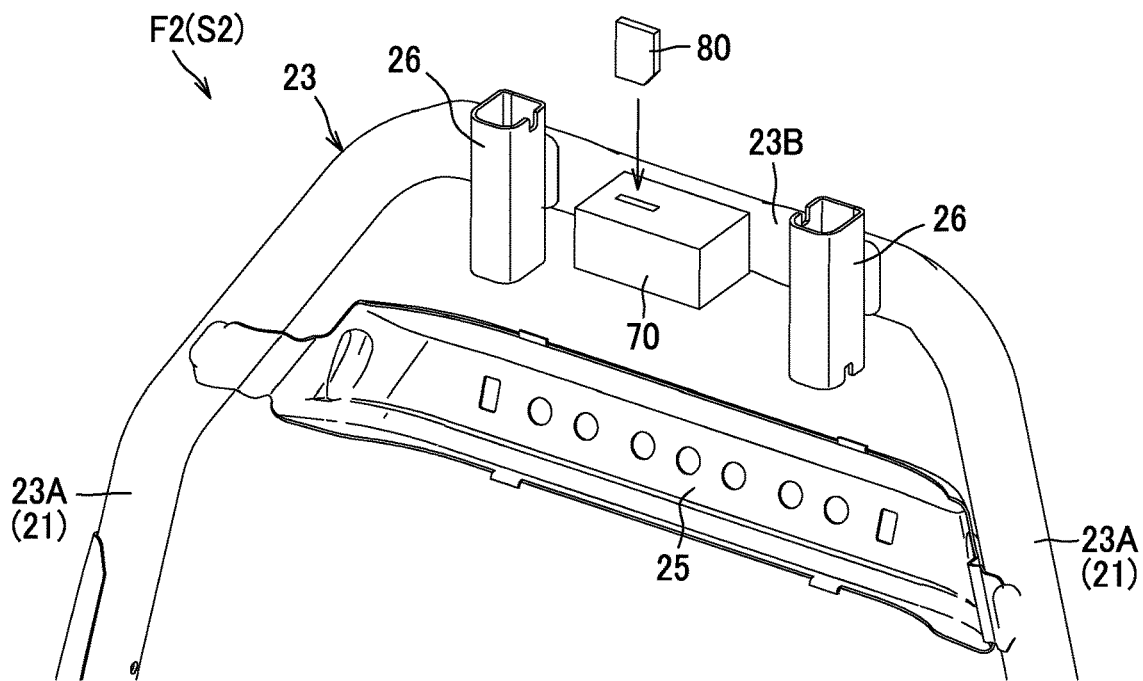
(b)
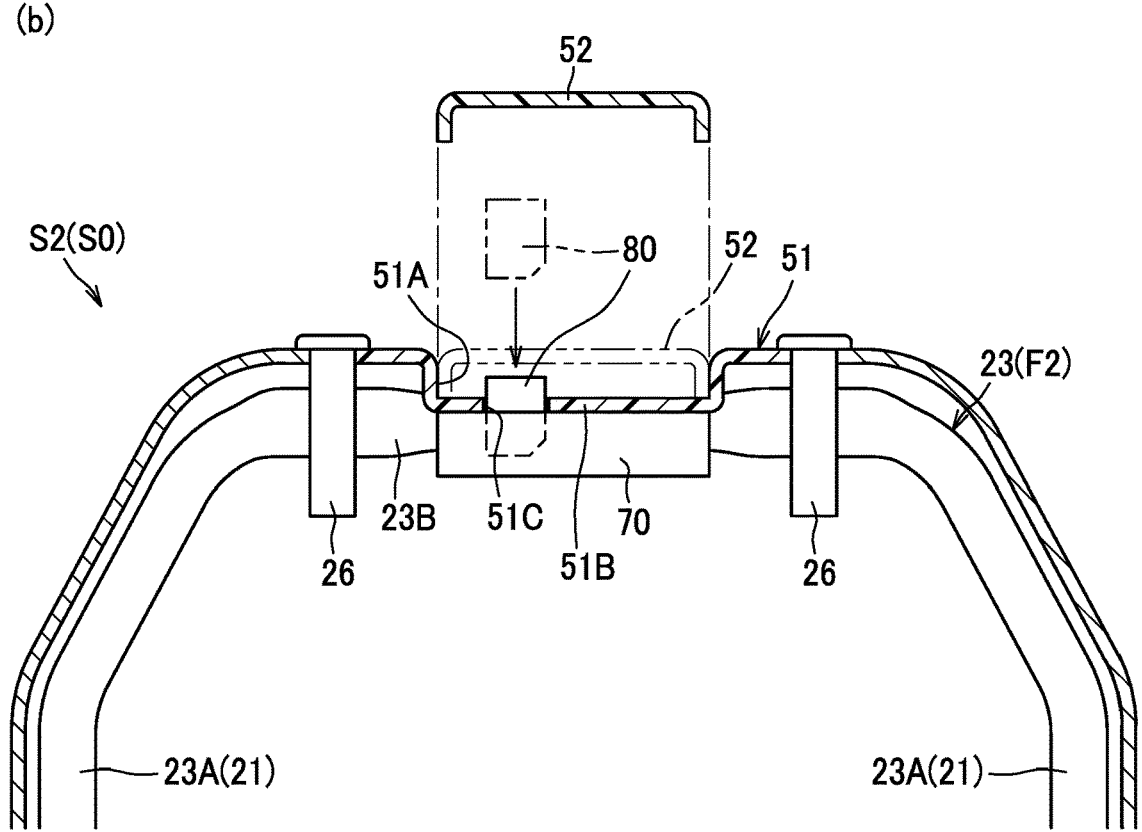

FIG.17
(a)
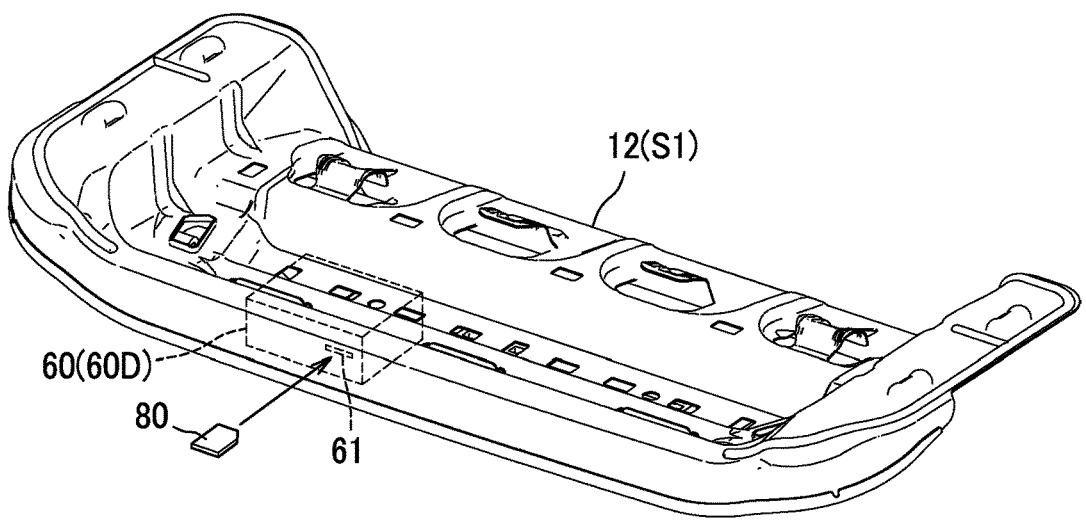
(b)
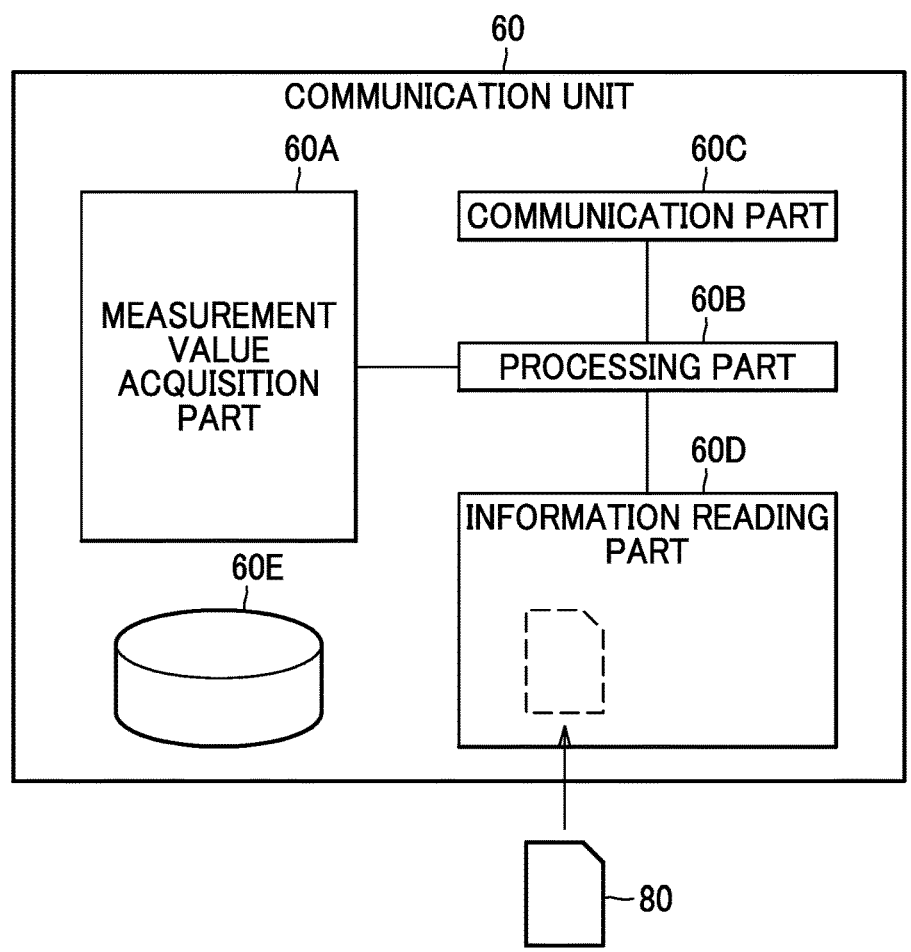

FIG.18
(a)
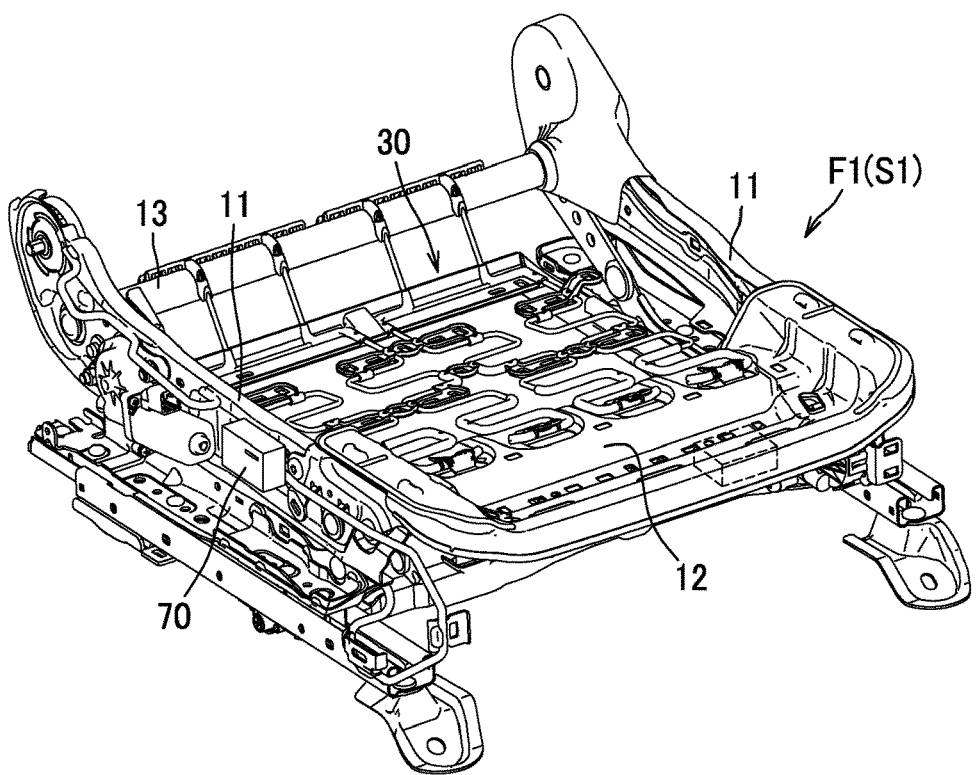
(b)
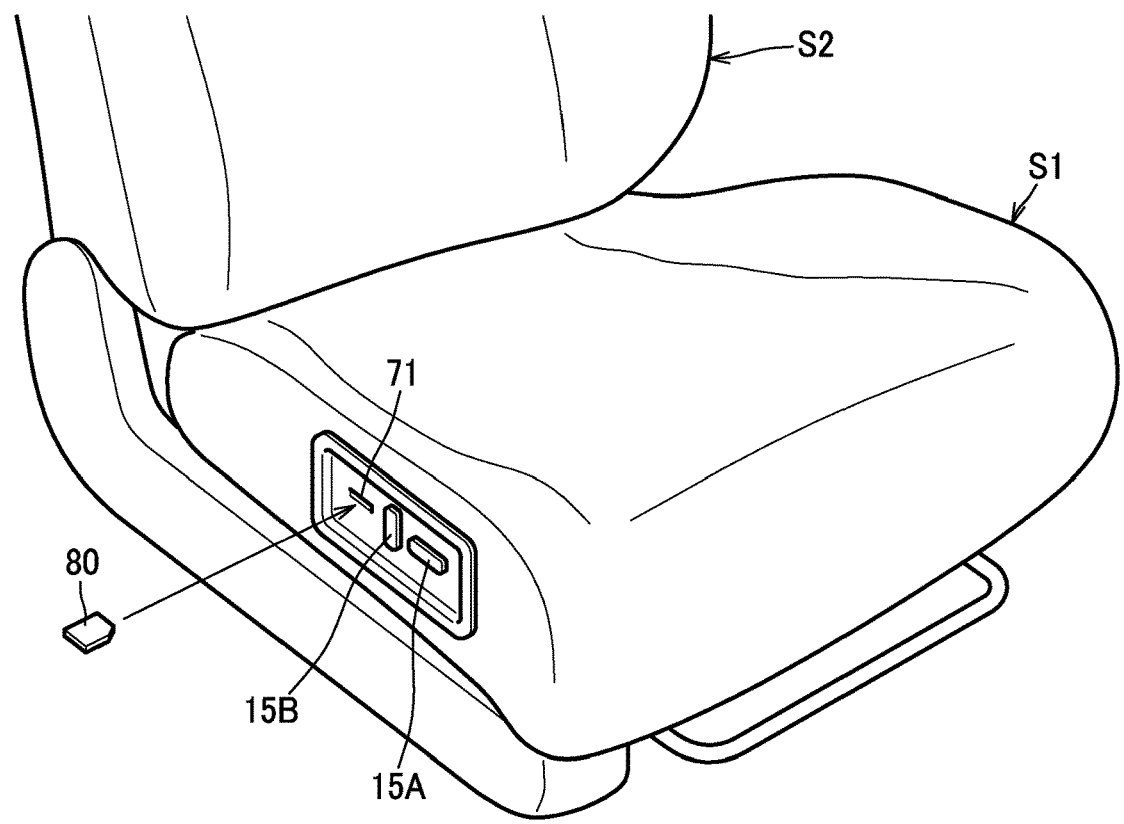

IN-SEAT EXPERIENCE SYSTEM

TECHNICAL FIELD

The present invention relates to an in-seat experience system offering increased versatility for proactive use of a seat and associated new values for an occupant.

BACKGROUND ART

An apparatus having a pressure sensor or the like provided in a driver's seat to evaluate a posture of a seated person is hitherto known in the art (Patent document 1).

CITATION LIST

Patent Literature

Patent document 1: JP H11-064131 A

SUMMARY OF INVENTION

However, the apparatus of Patent document 1 merely presenting the results of evaluation made on the posture of the seated driver disadvantageously does not appear to be utilized in its full potential. Inventors named in this application and their colleagues are contemplating utilizing the measurement values of sensors provided on the seat, to encourage an occupant seated in the seat to do physical exercise for promotion of health, and by extension to offer an occupant loyalty points for use in a specified region so that the local expense of such points promotes regional economy and plays a role in a business model established in association with the local development.

Against this backdrop, it is an object of the present invention to propose new values added to a seat, and to make good use of a seat with a sensor provided therein.

The present invention is made to solve the above-described problem and provides an in-seat experience system comprising: a seat which includes a seat body, a sensor provided in the seat body and configured to acquire a measurement value for use in identifying motion of an occupant seated on the seat body, and a seat controller connected to the sensor and thereby allowed to acquire the measurement value from the sensor; an experience instruction device connected to the seat controller, configured to notify an occupant seated on the seat body a motion instruction and to store user identification information for use in identifying the occupant; and a server capable of communicating with the experience instruction device. The experience instruction device is configured to make a determination based upon a measurement value of the sensor as to whether or not a first condition is satisfied, and to transmit a result of the determination to the server when at least the first condition is satisfied. The server is allowed to increase a point score stored for the corresponding user identification information with a condition that the result of the determination that the first condition is satisfied is received from the experience instruction device.

With this configuration, increase in a point score stored for the corresponding user identification information with a condition that the result of the determination that the first condition is satisfied is received from the experience instruction device by the server would possibly motivate the occupant to willingly utilize the experience instruction device for the purpose of earning points. Accordingly, the seat with a sensor provided therein can be utilized fully and effectively. It is to be understood that "points/point score" in the context of the present invention refers to a medium used within a specific community or between contracting parties to exchange commodities, services, etc., as provided under various names, etc. without limitation.

In the in-seat experience system described above, the server or the experience instruction device may be configured to make a determination as to whether or not a second condition different from the first condition is satisfied, wherein the server is configured to increase the point score if the first condition is satisfied and the second condition is satisfied, but not allowed to increase the point score if the first condition is satisfied but the second condition is not satisfied.

The occupant motivated by award point incentives would possibly continue to use the experience instruction device so as to earn allotted award points, but can be constrained from excessive use of the experience instruction device more than necessitated because, in order to have the point score increased (hereinafter also called "points granted"), the second condition is required to be satisfied. Moreover, The second condition can be defined as a condition linked with promotion of health, a condition requiring an occupant to go to a specified region, or like conditions that are stipulated with an objective beyond the normal use of the experience instruction device, so that the seat can be utilized effectively for the specified objective.

The server or the experience instruction device may be configured to make the determination as to whether or not the second condition is satisfied, based upon the measurement value of the sensor.

With this configuration in which the second condition is determined from the measurement value of the sensor, the determination as to grant of points can be made based on the state or motion of an occupant seated on the seat body.

The server or the experience instruction device may be configured to make the determination that the second condition is satisfied, if a period of time during which motion of the occupant is smaller than a predetermined scale, as determined from the measurement value of the sensor, is equal to or longer than a predetermined period of time.

Setting of the second condition like this can be exploited to invite an occupant sitting still in the seat to get exercise using the experience instruction device for promotion of the health of the occupant. Moreover, the situation in which the occupant keeps on moving to earn points can be relieved or prevented.

In the in-seat experience system described above, the sensor may be a pressure sensor. The server or the experience instruction device may be configured to make the determination that the second condition is satisfied, if a criterial time period determined as an accumulated period of time during which variations of the measurement value of the sensor fall within a range narrower than a predetermined range is equal to or longer than the predetermined period of time.

In an alternative configuration in which the sensor is a pressure sensor, the server or the experience instruction device may be configured to make the determination that the second condition is satisfied, if a criterial time period determined as a continuous period of time during which variations of the measurement value of the sensor fall within a range narrower than a predetermined range is equal to or longer than the predetermined period of time.

In the in-seat experience system described above, the server or the experience instruction device may be configured to reset the criterial time period after the server increases the point score.

In the in-seat experience system described above, the server or the experience instruction device may be configured to acquire location information of the seat, and to make the determination based upon the location information as to whether or not the second condition is satisfied.

With this configuration, for example, where the seat is a vehicle seat such as a car seat, the second condition defined based on the location information of the seat, such as requiring an occupant to go to a specified region may be set so that local development can be promoted and/or excessive use more than necessitated of the experience instruction device for the purpose of earning more points can be restricted.

Where determination as to the second condition is made based on location information, the server or the experience instruction device may be configured to compute a distance traveled of the seat based on the location information, and to make the determination that the second condition is satisfied, if the distance traveled is equal to or longer than a predetermined distance.

With this configuration, excessive use more than necessitated of the experience instruction device for the purpose of earning more points can be restricted. Furthermore, the traffic of persons can be made brisker, and the development of economy can be stimulated.

BRIEF DESCRIPTION OF DRAWINGS

FIG. 14 includes (a) a perspective view of a back side frame on which a card reader is mounted, and (b) a section view of a portion of the seat back around the card reader as viewed from front side.

FIG. 16 shows a third modified example of a seat, and includes (a) a perspective view of a part of the back frame of the seat and the card reader, and (b) a schematic diagram of an upper portion of a seat back.

FIG. 17 shows a fourth modified example of a seat, and includes (a) a perspective view of a pan frame and a communication unit of the seat, and (b) a block diagram of a communication unit of the seat.

FIG. 18 shows a fifth modified example of a seat, and includes (a) a perspective view of a cushion frame and a card reader of the seat, and (b) a section view of a part of the seat.

DESCRIPTION OF EMBODIMENTS

Next, a detailed description will be given of a first embodiment with reference made to accompanying drawings where appropriate.

Figure 1:
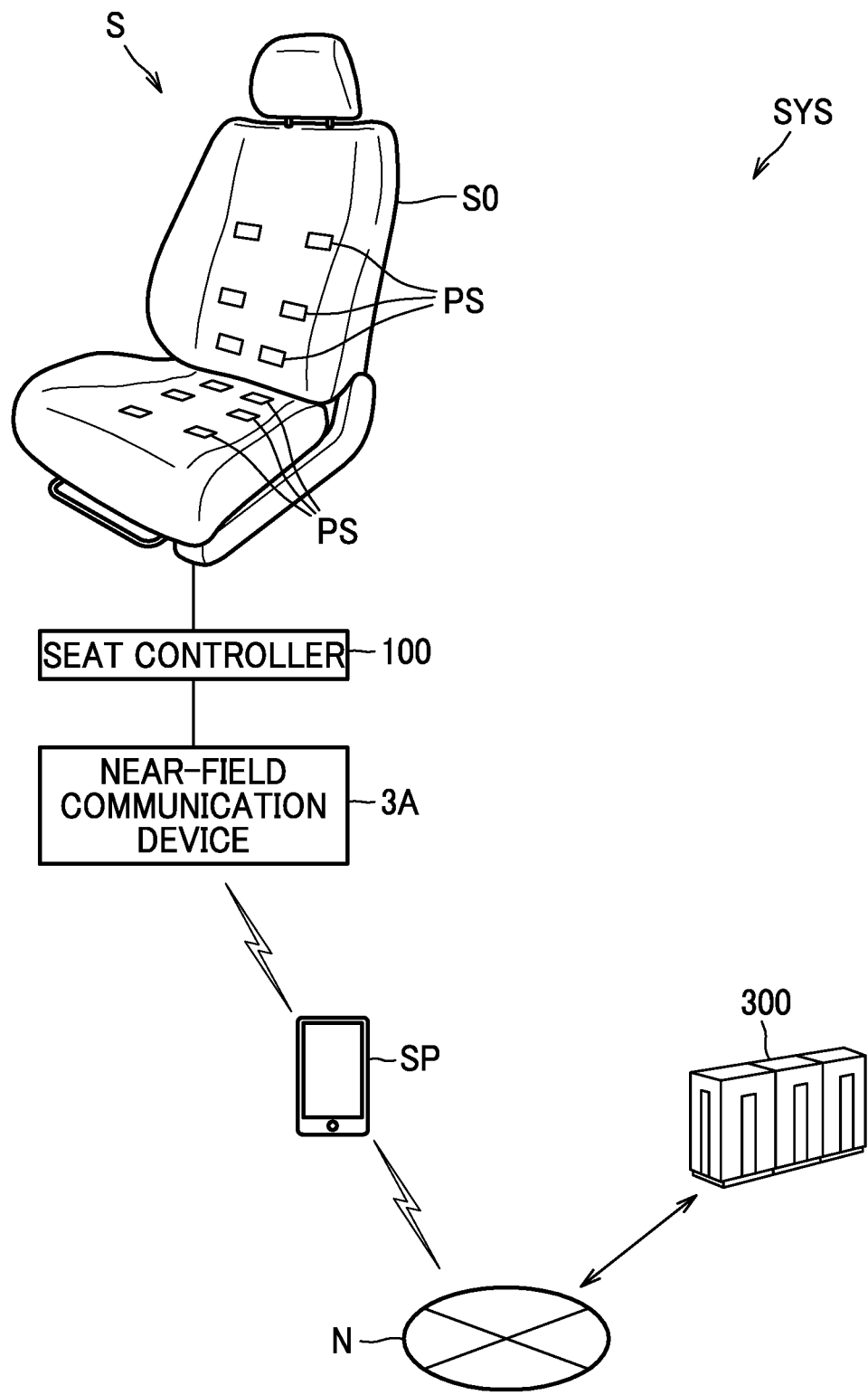
FIG. 1 is a diagram for explaining a general configuration of a system using a seat according to a first embodiment.

As shown in FIG. 1, an in-seat experience system SYS of the present embodiment includes a seat S, a seat controller 100, a smartphone SP as an example of an experience instruction device, and a server 300.

The seat S includes a seat body S0, pressure sensors PS (PS1 to PS6, see FIG. 3) as an example of a sensor provided in the seat body S0 and configured to acquire a measurement value for use in identifying motion of an occupant seated on the seat body S0, and a seat controller 100 connected to the pressure sensors PS and thereby allowed to acquire the measurement values from the pressure sensors PS.

The smartphone SP is connected to the seat controller 100 in a manner that allows the smartphone SP to communicate with seat controller 100 via a near-field communication protocol, configured to notify an occupant seated on the seat body S0 a motion instruction, and to store user identification information for use in identifying the occupant. Specifically, the smartphone SP is configured to be capable of providing a game to be played on the seat body S0 through execution of an application installed therein, and to notify an occupant a motion instruction by means of images or/and voices/sounds during the game process. The smartphone SP is connected to a network N such as the Internet and thus capable of network communication with other devices outside.

The server 300 is connected to the network N, and capable of communicating with the smartphone SP through the network N.

Figure 2:
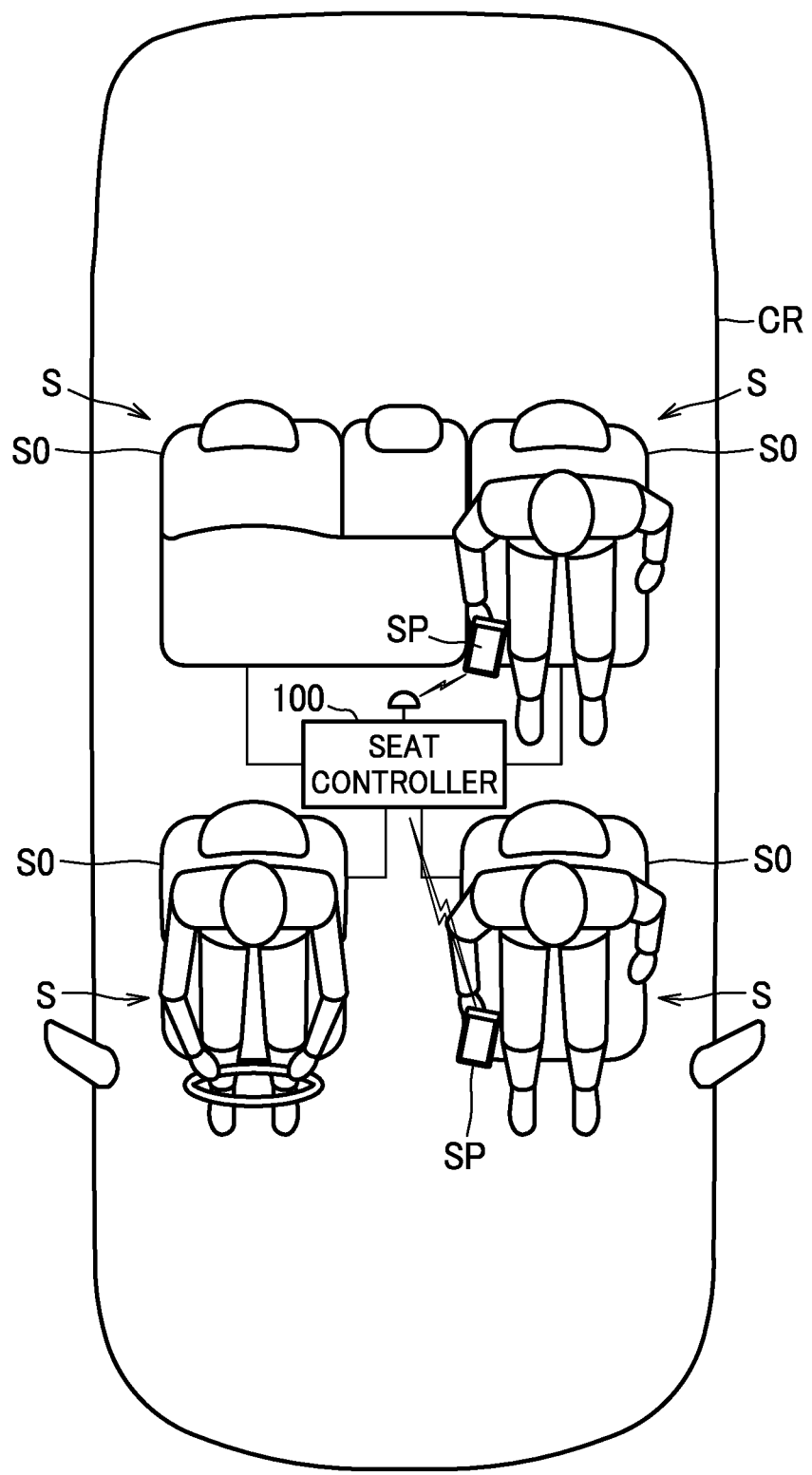
FIG. 2 is a diagram for showing arrangement of system components in an automobile.

As shown in FIG. 2, the seat S according to the present embodiment is configured as a car seat installed in a car CR. In the car CR, a plurality of seat bodies S0 are installed, and each of the seat bodies S0 is connected to a single seat controller 100.

Figure 3:
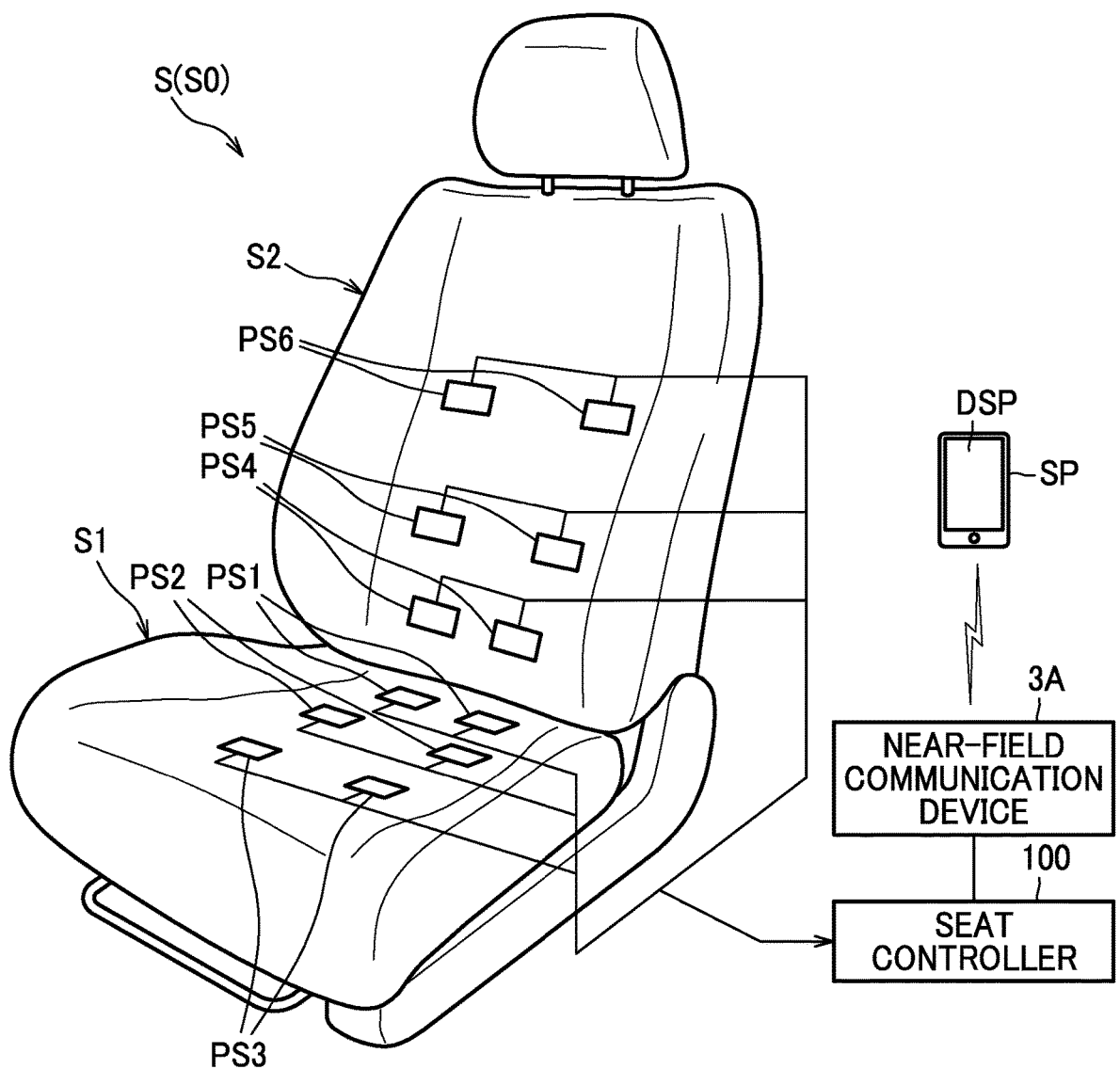
FIG. 3 is a diagram for explaining a configuration of each seat.

As shown in FIG. 3, the seat body S0 includes a seat cushion S1 and a seat back S2; pressure sensors PS1 to PS3 are provided under an outer covering of the seat cushion S1, and pressure sensors PS4 to PS6 are provided under an outer covering of the seat back S2. The respective pressure sensors PS1 to PS6 are provided in pairs, each located left and right, symmetric with respect to a laterally central position of the seat body S0.

The pressure sensors PS1, PS2 are located in positions corresponding to the buttocks of an occupant in the seat cushion S1. To be more specific, the pressure sensors PS1 are provided in positions which correspond to the lowermost portions of ischial bones of the occupant and on which the load of the occupant is borne largest; the pressure sensors PS2 are located a little frontward of the pressure sensors PS1. The pressure sensors PS1, PS2 are configured to acquire measurement values of pressure (hereinafter referred to also as "pressure values") from the buttocks of the occupant.

The pressure sensors PS3 are located frontward of and distanced far from the pressure sensors PS1 and the pressure sensors PS2, specifically, in positions corresponding to the thighs of the occupant. The pressure sensors PS3 are configured to acquire measurement values of pressure from the thighs of the occupant.

The pressure sensors PS4, PS5 are located in a lower portion of the seat back S2. To be more specific, the pressure sensors PS4 are located in positions corresponding to the back of the lumbar region of the occupant; the pressure sensors PS5 are located in positions a little higher than the positions of the pressure sensors PS4. The pressure sensors PS4, PS5 are configured to acquire measurement values of pressure from the lumbar region of the occupant.

The pressure sensors PS6 are located above and distanced far from the pressure sensors PS4, PS5, specifically, in positions corresponding to an upper part of the back of the occupant. The pressure sensors PS6 are configured to acquire measurement values of pressure from the upper part of the back of the occupant.

Connected to the seat controller 100 is a near-field communication device 3A which enables near-field communication, such as Bluetooth (registered trademark), Wi-Fi (registered trademark), etc. (see FIG. 1, FIG. 3). The seat controller 100 is configured to acquire pressure values from the pressure sensors PS1 to PS6 of each of the seat bodies S0 and transmit the same via the near-field communication device 3A to the smartphone SP.

The pressure sensors PS1 to PS6 are each configured, for example, as an element whose electrical resistance varies with external pressure applied thereto, wherein the larger the pressure value, the higher (or the lower, as the case may be) the voltage of the detection signal becomes. Accordingly, in practical applications, the magnitude of the pressure values are compared with reference made to the magnitude of the voltage values; however, for easy understanding, this specification is described as if comparison is made based on the magnitude of the pressure values.

Figure 4:
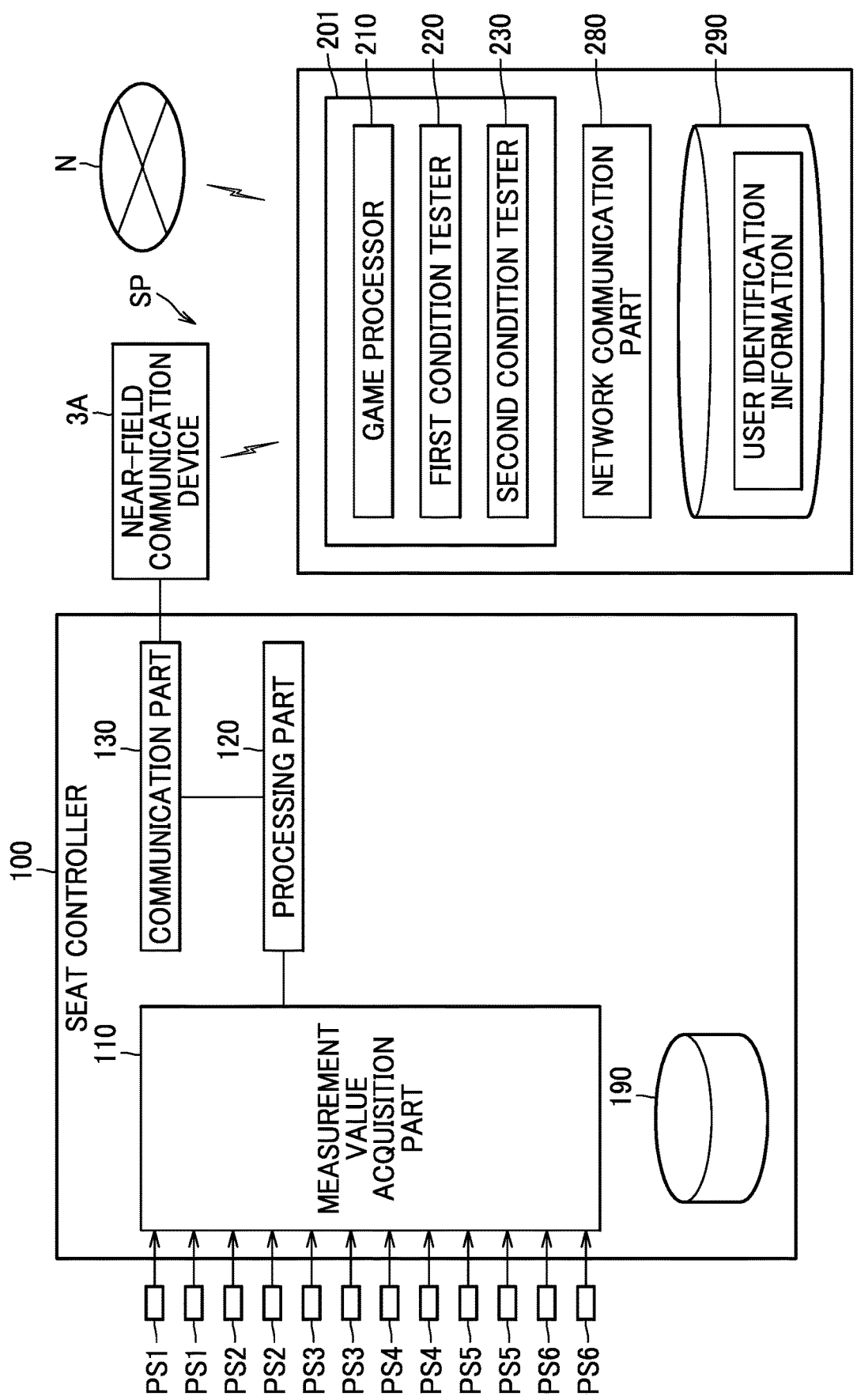
FIG. 4 is a block diagram for explaining configurations of a seat controller and a smartphone.

As shown in FIG. 4, the seat controller 100 comprises a measurement value acquisition part 110, a processing part 120, a communication part 130, and a storage part 190. The seat controller 100 includes a CPU, a ROM, a RAM, a rewritable nonvolatile memory, etc., which are not illustrated in the drawings; each functional part is implemented through execution of pre-stored programs.

The measurement value acquisition part 110 has a function of acquiring measurement values of pressure per given control cycle from the respective pressure sensors PS1 to PS6. The measurement values acquired by the measurement value acquisition part 110 are stored in the storage part 190 and used in the processing part 120. The storage part 190 is used to store data required for computation, processing, etc., on an as-appropriate basis.

The processing part 120 subjects measurement values acquired in the measurement value acquisition part 110 to analogue-to-digital conversion. The thus-digitized measurement values are transmitted via the communication part 130 to the smartphone SP.

The smartphone SP has a game app 201 installed therein. The game app 201 comprises a game processor 210, a first condition tester 220, and a second condition tester 230. The smartphone SP comprises a network communication part 280 and a storage part 290. The smartphone SP includes a CPU, a ROM, a RAM, a rewritable nonvolatile memory, etc., which are not illustrated in the drawings; each functional part is implemented through execution of pre-stored programs. The smartphone SP has a near-field communication capability (not shown) and is thus capable of communicating with the seat controller 100. Furthermore, the smartphone SP can establish connection via the network communication part 280 to the network N, and is configured to be capable of communicating with the server 300 (see FIG. 1) based on predetermined communication settings.

When the game app 201 is started, the game processor 210 executes the process of a game and ending of the game. After the game ends, the game processor 210 causes the first condition tester 220 and the second condition tester 230 to make a determination as to whether to grant points, and if the conditions for granting the points are satisfied, transmits to the server 300 an instruction to grant the points.

The game processor 210 is a unit configured to provide a motion instruction via a display DSP (see FIG. 3) and a speaker (not shown) of the smartphone SP, and to provide a game to an occupant. The motion instruction herein is not limited to any particular contents, and may include, for example: instructions to lift foots alternately, and to twist his/her upper body left or right, etc. The instruction may be provided at the beginning of the game by means of text characters or voices/sounds as guidance information, or may be shown on the display at a specific time in the process of the game by means of an image indicating a body part to be moved.

In the present embodiment, as the contents, etc. of the game are not important, a simple example of a game is shown, in which an instruction to quickly lift feet alternately is given and the number of steps (the number of times of lifting feet) for 10 seconds are counted for competition.

Figure 6:
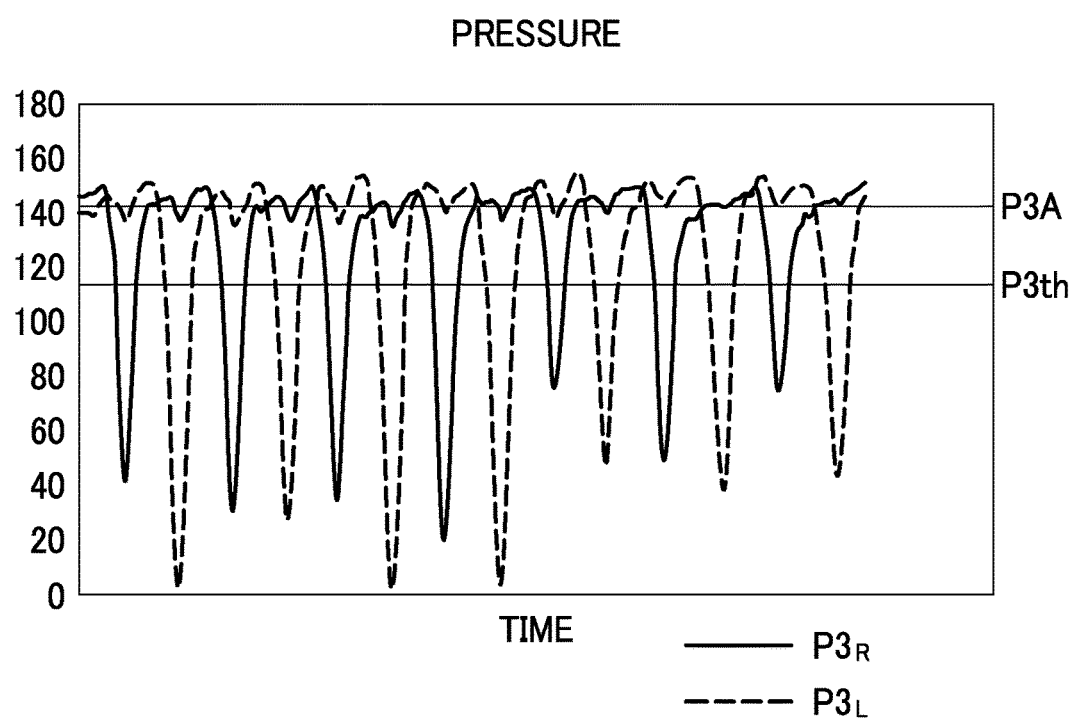
FIG. 6 is a graph showing change of pressure value acquired by a pressure sensor, as effected when foots are lifted alternately.

FIG. 6 shows an example of measurement values of the pressure sensors PS3 acquired when an occupant lifts his/her feet alternately in the seat S. $P3_R$ indicates a pressure value of the right pressure sensor PS3, and $P3_L$ indicates a pressure value of the left pressure sensor PS3. As the measurement values represent, lifting of the feet causes transitory drops of $P3_R$ and $P3_L$; therefore, peaks of $P3_R$ and $P3_L$ may be detected, so that a determination that one step is taken may be made when a peak is detected. Peak detection may be made, for example, in the following manner. A mean value P3A of $P3_R$ and $P3_L$ are calculated from measurement values acquired for that occupant when seated in the seat (before starting the competition), and a threshold value P3th is set at a value reduced by a predetermined rate from the calculated mean values as a preparation. The determination that the measurement value has reached a peak can be made at a time when $P3_R$ or $P3_L$ starts to increase after dropping below the threshold value P3th.

After the application of the smartphone SP is launched, the game processor 210 provides a predetermined guide for the game by means of voices/sounds or an image, and notifies an occupant of a start of the competition with the voices/sounds and image signaling the start, while turning on a timer. After the timer starts counting up, the game processor 210 detects peaks for 10 seconds based on the pressure values received from the seat controller 100. Then, the number of steps, i.e., the number of peaks, is shown on the display DSP as "step count" that is the result of the game.

The first condition tester 220 makes a determination as to whether or not a first condition is satisfied, based on measurement values of the pressure sensors PS3. In the present embodiment, the first condition is that the step count as the result of the game is equal to or more than a predetermined step count (e.g., 40 steps or more). The first condition tester 220 causes the result of determination to be stored in the storage part 190 as occasion arises.

The second condition tester 230 makes a determination as to whether or not a second condition different from the first condition is satisfied. In the present embodiment, the second condition is that a period of time during which motion of the occupant is smaller than a predetermined scale, as determined from the measurement values of the pressure sensors PS3, is equal to or longer than a predetermined period of time. To be more specific, this predetermined period of time is an accumulated period of time, and the second condition is that a criterial time period TJ determined as an accumulated period of time during which variations of the measurement values of the pressure sensors PS3 fall within a range narrower than a predetermined range is equal to or longer than the predetermined period of time (threshold value TJth).

Figure 7:
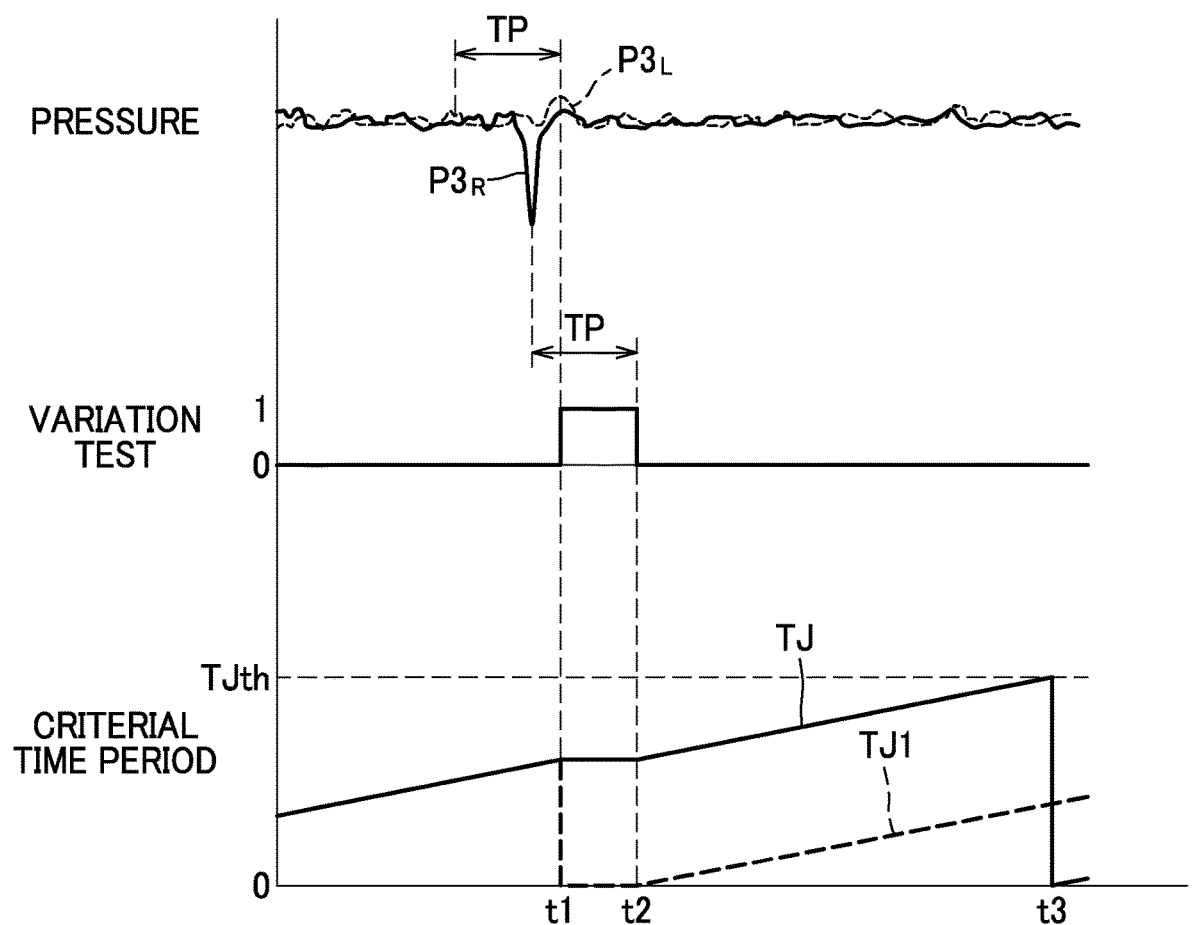
FIG. 7 is a time chart showing a pressure value, a result of determination as to pressure value variations and a criterial time period.

Determination of such variations can be made, for example, in the following manner. FIG. 7 is a time chart showing change of pressures $P3_R$ and $P3_L$ measured when an occupant is seated, a result of determination as to whether or not the variations are detected, and a criterial time period TJ. Whether or not the variations are detected can be determined by comparison made at a time of determination, i.e., for the immediately preceding time frame of a predetermined time period TP, of a difference between the maximum value and the minimum value of $P3_R$ and $P3_L$ with a predetermined value; if the difference is equal to or greater than the predetermined value, then it is determined that the variations are detected (the result evaluated as 1 in FIG. 7), while if the difference is smaller than the predetermined value, then it is determined that the variations are not detected (the result evaluated as 0 in FIG. 7). In the example shown in FIG. 7, at a time t1, the difference between the maximum value and the minimum value of $P3_R$ and $P3_L$ for the predetermined time period TP immediately preceding the time t1 becomes equal to or greater than the predetermined value, and the variation test result is set at 1; at a time t2, the difference between the maximum value and the minimum value of $P3_R$ and $P3_L$ for the predetermined time period TP immediately preceding the time t2 becomes smaller than the predetermined value, and the variation test result is set at 0.

The second condition tester 230 conducts this variation test, and if the variation test result shows 0, starts measuring a lapse of the criterial time period TJ, and if the variation test result shows 1, stops measuring a lapse of the criterial time period TJ. When the criterial time period TJ reaches the threshold value TJth, the second condition tester 230 makes a determination that the second condition is satisfied. After the server 300 grants points (increases point score), the second condition tester 230 resets the criterial time period TJ (t3).

The second condition tester 230 causes the variation test results and the determined criterial time period to be stored in the storage part 290 as occasion arises.

When the first condition tester 220 and the second condition tester 230 determine that both of the first condition and the second condition are satisfied, the game app 201 transmits to the server 300 an instruction to grant the points. The storage part 290 stores user identification information for use in identifying users, and the game app 201 transmits the user identification information, when transmitting an instruction to grant the points, to the server 300. The user identification information may be any unique user-identifiable data, without limitation, which may be in the form of simple numeric, alpha-numeric character string, e-mail address, telephone number, etc.

Figure 5:
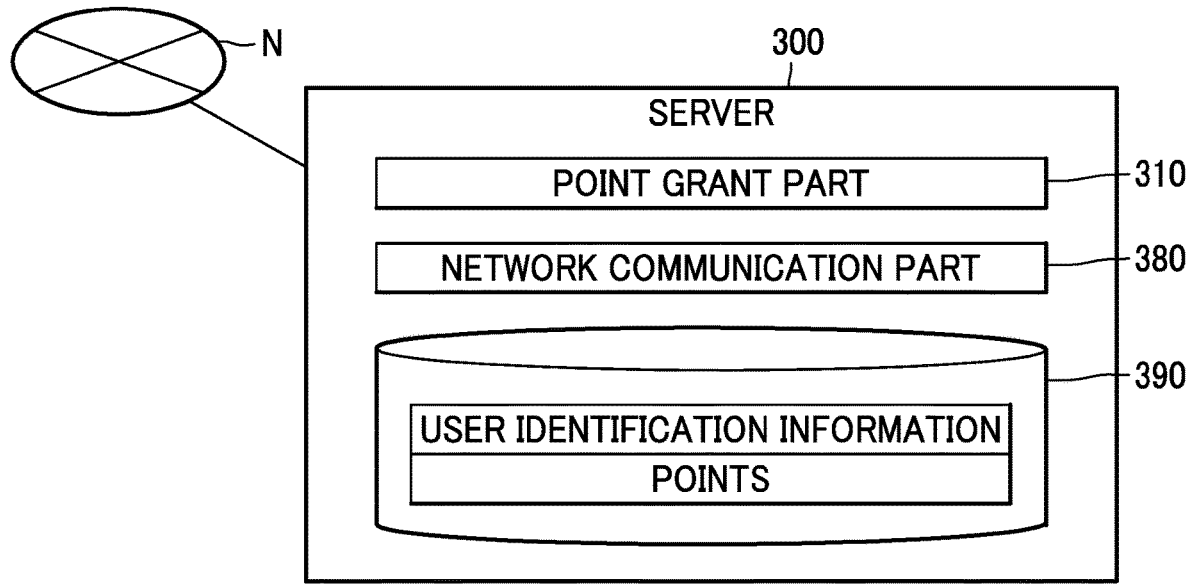
FIG. 5 is a block diagram for explaining a configuration of a server.

As shown in FIG. 5, the server 300 includes a point grant part 310, a network communication part 380, and a storage part 390. The server 300 is connected via the network communication part 380 to the network N, and capable of communicating with the smartphone SP via the network N. The storage part 390 stores data necessary for operation of the server 300 on an as-appropriate basis, and also stores points associated with user identification information (the point score for each user specified by the corresponding user identification information).

Upon receipt of an instruction to grant points from the smartphone SP, the point grant part 310 increases, in a predetermined increment, a point score corresponding to specific user identification information included in the instruction to grant the points. The point score to be increased may be a fixed value, or may vary according to times, seasons, user types, etc.

The event that the server 300 receives an instruction to grant points takes place when the first condition is satisfied and the second condition is satisfied at the same time. That is to say, the server 300 is allowed to increase a point score stored for the corresponding user identification information with a condition (necessary condition) that the result of the determination that at least the first condition is satisfied (instruction to grant points) is received from the smartphone SP. Moreover, the server 30 is configured to increase the point score if the first condition is satisfied and the second condition is satisfied (i.e., when the instruction to grant points are received), but not allowed to increase the point score if the first condition is satisfied but the second condition is not satisfied.

When the point score stored for the corresponding user identification information is increased, the point grant part 310 transmits to the smartphone a message signal to that effect.

A description will be given of a general operation of the in-seat experience system SYS configured as described above with reference to the flowchart of FIG. 8.

Figure 8:
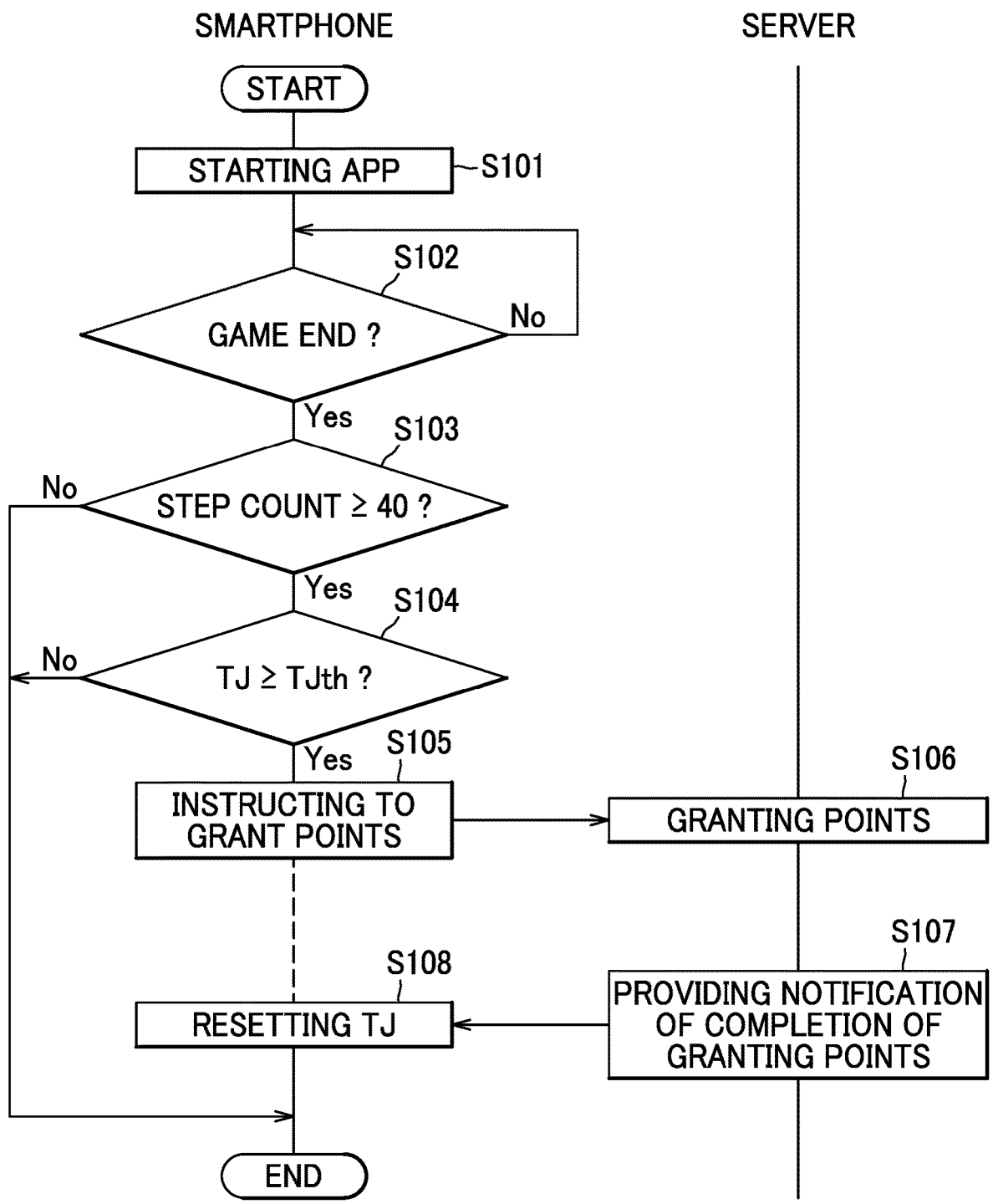
FIG. 8 is a flowchart showing processes in the smartphone and the server.

As shown in FIG. 8, when a predetermined game app 201 is started in the smartphone SP (S101), the game processor 210 starts the process of a foot-lift exercise game. When this ten-second game comes to an end (Yes, S102), the first condition tester 220 makes a determination as to whether or not the step count is equal to or more than 40 (whether or not the first condition is satisfied) (S103). If the step count is less than 40 (No, S103), then the game app 201 brings the process to an end. If the step count is equal to or more than 40 (Yes, S103), then the second condition tester 230 makes a determination as to whether or not the criterial time period TJ is equal to or greater than the threshold value TJth (S104). If TJ<TJth (No, S104), then the game app 201 brings the process to an end. If TJ≥TJth (Yes, S104), then the game app 201 transmits to the server 300 an instruction to grant points (S105).

The server 300 receives this instruction to grant points, and increases a point score stored for the corresponding user identification information (S106). The server 300 then transmits a notification of completion of granting points to the smartphone SP (S107).

The game app 201, upon receipt of the notification of completion of granting points, resets the criterial time period TJ (S108), and brings the process of the game to an end.

As described above, according to the in-seat experience system SYS of the present embodiment, increase in a point score stored for the corresponding user identification information with a condition that the result of the determination that the first condition is satisfied is received from the smart phone SP by the server 300 would possibly motivate the occupant to willingly utilize the smartphone SP for the purpose of earning points. Accordingly, the seat S with pressure sensors PS provided therein can be utilized in its full potential.

The occupant motivated by award point incentives would possibly continue to use the smartphone SP so as to earn allotted award points, but can be constrained from excessive use of the smartphone SP more than necessitated because, in order to have points granted, the second condition is required to be satisfied.

On the contrary, since the occupant after a while seated still is allowed to earn points, the occupant can become willing to play the foot-lift game in order to earn points; therefore, poor blood circulation can be made unlikely to occur to the advantage of promotion of health.

According to the present embodiment, in which the second condition is tested based on the measurement values of the pressure sensors PS, a determination as to whether to grant points can be made based on the sitting state or motion of the occupant on the seat body S0. Therefore, the motion of the occupant in the vehicle can be controlled indirectly by enhancing the occupant's motivation to have points granted, to the advantage of promotion of health.

Although the embodiment has been described above, this embodiment may be implemented with partial modifications made to its configuration.

For example, although the determination that the second condition is satisfied is made in this embodiment if the criterial time period TJ determined as an accumulated period of time during which variations of the measurement values of the pressure sensors PS3 fall within a range narrower than a predetermined range is equal to or longer than the predetermined period of time (threshold value TJth), the criterial time period TJ may be determined as a continuous period of time during which variations of the measurement values of the pressure sensors PS3 fall within a range narrower than a predetermined range, and the determination that the second condition is satisfied may be made if this criterial time period TJ is equal to or longer than the predetermined period of time. In this alternative configuration, the smartphone SP resets the criterial time period TJ when the variation test results in 1, as FIG. 7 shows in the graph (broken line) of the criterial time period TJ.

Although the determination as to whether the first condition is satisfied (the process of the game) and the determination as to whether the second condition is satisfied in this embodiment are made by using the pressure sensors PS3 only, the other pressure sensors PS1, PS2, PS4 to PS6 may be used.

Although the determination as to whether the second condition is satisfied in this embodiment is executed by the smartphone SP as an experience instruction device, an alternative configuration may be feasible such that the information necessary to test the second condition is transmitted from the experience instruction device to the server 300 and the server 300 executes the determination as to whether or not the second condition is satisfied. In this alternative configuration, the criterial time period TJ may be reset by the server 300.

Although the determination as to whether the second condition is satisfied in this embodiment is made based on the measurement values of the sensors, the smartphone SP may be configured to make a determination as to whether or not the second condition is satisfied, based on location information of the seat S.

For testing the second condition based on the location information, for example, the smartphone SP may be configured to compute a distance traveled of the seat S based on the location information, and to make the determination that the second condition is satisfied, if the distance traveled is equal to or longer than a predetermined distance.

The location information may be acquired from a GPS (global positioning system) with which a commonly-used smartphone may be equipped. It is also quite likely that the car CR or the seat body S0 is equipped with GPS from which the location information may be acquired.

The game app 201 then stores location information acquired on the last occasion of instruction to grant points (this location information is hereinafter referred to as the last location information G), and computes, as a travel distance D, a distance between the current location determined when the game comes to an end and the stored last location G. If the travel distance D is equal to or greater than a threshold value Dth, the second condition tester 230 makes a determination that the second condition is satisfied.

Figure 9:
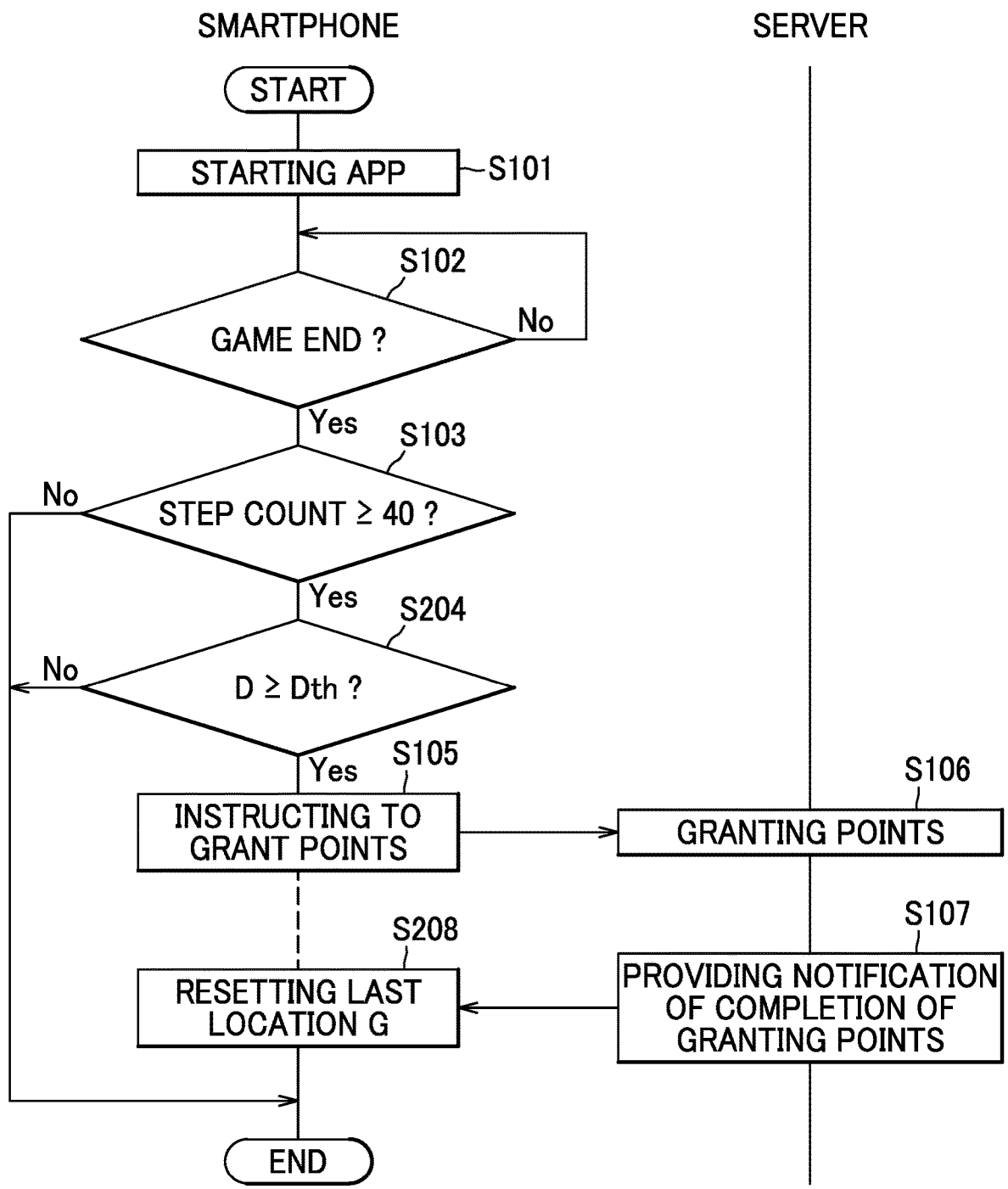
FIG. 9 is a flowchart followed when determination as to a second condition is made based on location information.

The flowchart of this configuration is shown in FIG. 9.

The flowchart of FIG. 9 shows a modified example in which steps S104 and S108 in the flowchart of FIG. 8 are changed.

When the game comes to an end in the smartphone SP (Yes, S102) and the first condition tester 220 makes a determination that the step count is equal to or more than 40 (Yes, S103), then the second condition tester 230 computes a travel distance D as a distance in a straight line between the last location G and the current location, and makes a determination as to whether or not the travel distance D is equal to or greater than the threshold value Dth (S204). If D<Dth (No, S204), then the process is brought to an end, while if D≥Dth (Yes, S204), then an instruction to grant points is transmitted to the server 300 (S105).

The game app 201, upon receipt of the notification of completion of granting points, resets the last location G, i.e., overwrites it with the current location, and stores the current location in the storage part 290 (S208).

In this way, the second condition may be defined based on the location information as satisfied when a distance traveled from the last location G is equal to or longer than a distance of the threshold value Dth, and the grant of points may be provided conditionally on satisfaction of both of the first condition and the second condition. Accordingly, excessive use more than necessitated of the experience instruction device for the purpose of earning more points can be restricted. Furthermore, the traffic of persons can be made brisker, and the development of economy can be stimulated.

In this configuration, the travel distance D computed may not be a distance in a straight line but a distance measured along a path. In this alternative example, the game app 201 may be configured to compute, at specific time intervals, travel distance (distance in a straight line between a last location as measured the specific time interval before and a present location) and add up the travel distances computed to obtain the travel distance D.

In this configuration, computation of the distance and determination may not be performed by the experience instruction device (smartphone SP) but may be performed by the server. For example, the server may be configured to acquire location information periodically from the experience instruction device to compute a travel distance D, and to make a determination as to whether or not the travel distance D is equal to or greater than the threshold value Dth (whether or not the second condition is satisfied).

In this configuration, the second condition is defined as satisfied when a travel distance D is equal to or longer than a predetermined distance, but the second condition defined based on location information such as satisfied when an occupant (seat S) is located in a specific geographical area may also be feasible. In this way, setting the second condition based on the location of the seat S would entice potential customers to come into a specified region, so that local development can be promoted.

The present invention may further be implemented in other forms.

For example, the second condition may be defined based on location information as satisfied when the car is stuck on a gridlocked highway. With this configuration, one who is stuck on a gridlocked highway and has too much time hanging heavy on hands can take advantage of this opportunity to get physical exercise to thereby improve health.

Alternatively, the second condition may be defined as requiring a use of the seat for a specific objective, e.g., use as a training machine. With this configuration as well, improvement of health can be achieved by the use of a seat.

Alternatively, the app of the experience instruction device may be configured to instruct a user to move his/her feet, and the second condition may be defined as satisfied when the number of steps for one day set for each user is reached. In this alternative configuration as well, an occupant can be motivated to move his/her feet willingly, so that improvement of health can eventually be achieved.

The in-seat experience system may be configured to place limitations on its own function when a predetermined state, such as an abnormal event, is detected. When such limitations are placed in practice, only part of its function may be disabled, or its function may be totally disabled.

Examples of the abnormal event may include anomalies in various sensors in the seat, a break or other anomalies in a harness of the seat, an anomaly of the seat controller (ECU), an anomaly in communication, an anomaly in equipment, such as a server, at the other end in the communication network, and an anomaly in an actuator, such as a motor. The abnormal event may include an event found anomalous in the external environment. Such abnormal event in the external environment may include, for example: an approach of another vehicle, bad wheeling road condition, vehicle speed greater than a predetermined value, a strike of an earthquake, destination approaching, the destination having been reached already, it turned out that the game will not come to an end before reaching a destination, the fuel about to run out, the battery about to run down, the temperature or humidity too high in the vehicle or outside, etc.

The contents of the limitations to be placed may include: disabling part of the features of the game, effecting forced termination of the game, issuing a notification of recommendation to exit the game, etc. Examples of disabling part of the features of the game may include, for example, for a 100-meter dash game, allowing historical data, etc. to be perused but not allowing a user to run in a race, etc.

The contents of the limitations may be configured to vary with the level of the abnormality. For example, if not every sensor is found faulty, only the relevant part of the features may be restricted; if the seat controller shows abnormalities, the game may be terminated forcefully; if road condition is bad, a recommendation to exit the game may be notified.

Under circumstances where limitations are placed on the features of the app due to any abnormal event, the grant of award points may be prohibited. Alternatively, points may be calculated and granted based on a track record prior to the abnormal event.

A further optional configuration feasible may be such that when the seat controller makes a determination that any abnormal event occurs, the seat controller provides notification of the abnormal event to the manufacturer of the seat or the manufacturer of the car.

The server may be configured to grant points when the second condition is not satisfied. Even with this configuration, an occupant who expects to have points granted if the first condition is satisfied can be motivated to make full use of the seat with sensors provided therein.

An additional configuration may be feasible in which still another condition for having points granted is required to be satisfied. For example, the condition that the in-seat experience is enjoyed simultaneously by fellows may be required. Such additional condition(s) may be attached not as requirements for granting points but as requirements for adding extra points (so-called bonus points as a premium). To this end, association data, indicating correlations between one experience instruction device of one user (user identification information) and other experience instruction devices of his/her fellow users (user identification information), i.e., data correlated in terms of fellowship recognized by the users, may be stored in the server.

Although the sensor is exemplified by pressure sensors in the above-described embodiment, the sensor may be any other types of sensors, e.g., capacitance sensors or the like. Alternatively, the sensor may be a temperature sensor.

The experience instruction device may be a navigation system provided fixedly in the vehicle. That is, the existing navigation system may be provided with game implementing features which produces a motion instruction, and used as an experience instruction device.

Although the seat controller and the smartphone in the above-described embodiment are connected via radio communication, they may be connected by wire.

The experience instruction device may be configured partly or entirely to be integral with the seat controller in appearance.

The car seat installed in a car of an automobile is described by way of example in the above-described embodiment; however, the seat may be for a vehicle other than an automobile, such as a railcar, or for a vehicle other than a car, such as a ship, an aircraft, a rocket, etc. Furthermore, any such seats as installed in a house, or facilities, etc. may also be consistent.

Next, a description will be given of another type of seat, different from the seat S for the in-seat experience system according to the first embodiment, such that a communication capability is provided in the seat itself.

Conventionally, a structural improvement in arrangement of a plurality of seats in a car for the purpose of facilitating better communications among passengers is known in the art (see JP 2018-020738 A).

However, it is to be understood that the future seat should be a device that enables more progressive communications.

In this respect, a seat capable of identifying an individual seat which is then allowed to establish radio communication is provided herein.

It is an object to transmit information based on a measurement value of a sensor provided in a seat body to a device outside the seat body.

It is another object to provide an information reading part in a stable state.

It is still another object to protect an information reading part or the like while allowing a recording medium to be inserted therein and ejected therefrom.

It is still another object to allow a recording medium to be inserted and ejected easily.

A seat provided to achieve any of the objects described above comprises a seat body, a radio communication part capable of radio communication with a device outside the seat body, and an information reading part provided in the seat body and connected to the radio communication part, wherein a recording medium with identification information recorded therein to enable radio communication by the radio communication part is insertable in and ejectable from the information reading part, which is capable of reading the identification information when the recording medium is inserted therein.

With this configuration, an individual seat can be identified by the identification information recorded in the recording medium and then radio communication can be established with a device outside the seat body.

The seat described above may comprise a sensor provided in the seat body, wherein the radio communication part is connected to the sensor in a manner that enables acquisition of a measurement value of the sensor, and is capable of transmitting information based on the measurement value to the device outside the seat body.

With this configuration, information based on a measurement value of the sensor provided in the seat body can be transmitted to the device outside the seat body.

In the seat described above, the seat body may be configured to comprise a seat frame, wherein the information reading part is attached to the seat frame.

With this configuration, the information reading part can be provided in the seat body in a stable state.

In the seat described above, the seat frame may be configured to have a first slot hole which permits the recording medium to pass therethrough to be inserted in and ejected from the information reading part.

With this configuration, the information reading part can be protected by the seat frame while a recording medium can be inserted in and ejected from the information reading part through the first slot hole.

The seat described above may be configured such that the seat body includes a panel exposed on outside with a second slot hole which permits the recording medium to pass therethrough to be inserted in and ejected from the information reading part, and a cover capable of being shifted in position to a state in which the second slot hole is covered therewith and to a state in which the second slot hole is uncovered.

With this configuration, the information reading part and/or a recording medium inserted therein can be protected by the panel and the cover while a recording medium can be inserted in and ejected from the information reading part through the second slot hole.

In the seat described above, the information reading part may be provided in a seat back of the seat body.

In the seat described above, the seat back may comprise a pair of back side frames which constitute left and right frames of the seat back, and the information reading part may be attached to one of the pair of back side frames.

With these configurations, the information reading part can be provided in the seat back in a stable state.

In the seat described above, the seat back may comprise a pair of back side frames which constitute left and right frames of the seat back, and a connecting frame which connects the pair of back side frames, and the information reading part may be attached to the connecting frame.

With this configuration, the information reading part can be provided in the seat back in a stable state.

In the seat described above, the seat back may comprise a pair of brackets to which a pair of pillars of a headrest are mounted, and the information reading part may be disposed between the pair of brackets.

With this configuration, the information reading part can be disposed at the upper part of the seat back to which the headrest is to be mounted, so that the recording medium can be inserted in and ejected from the information reading part with ease.

In the seat described above, the information reading part may be provided in a seat cushion of the seat body.

In the seat described above, the seat cushion may comprise a pair of cushion side frames which constitute left and right frames of the seat cushion, and a pan frame which connects the pair of cushion side frames, and the information reading part may be attached to the pan frame.

With this configuration, the information reading part can be provided in the seat cushion in a stable state.

In the seat described above, the seat cushion may comprise a pair of cushion side frames which constitute left and right frames of the seat cushion, and the information reading part may be attached to one of the pair of cushion side frames.

With this configuration, the information reading part may be provided in the seat cushion in a stable state.

In the seat described above, the recording medium may be configured as an IC card.

In the seat described above, the IC card may be configured as a SIM card.

Hereafter, a detailed description will be given of a second embodiment in which a communication capability is provided in a seat itself, with reference to FIGS. 10 to 19.

Figure 10:
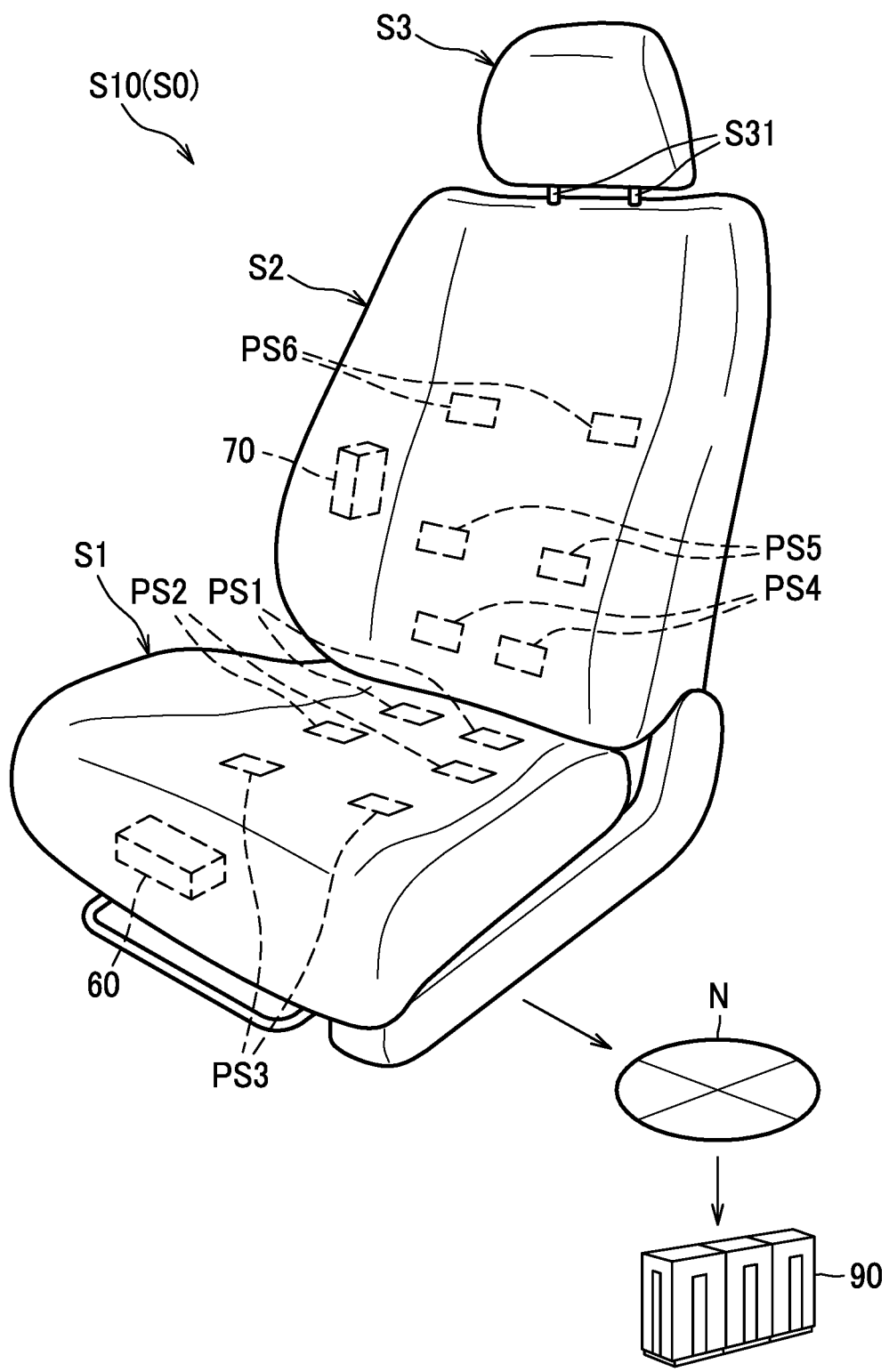
FIG. 10 is a perspective view of a seat according to a second embodiment.

As shown in FIG. 10, a seat S10 is configured as a car seat installed in an automobile. The seat S10 includes a seat body S0 for a person (occupant) to be seated thereon, a plurality of pressure sensors PS1 to PS6 as an example of a sensor, a communication unit 60 as an example of a radio communication part, and a card reader 70 as an example of an information reading part.

Figure 11:
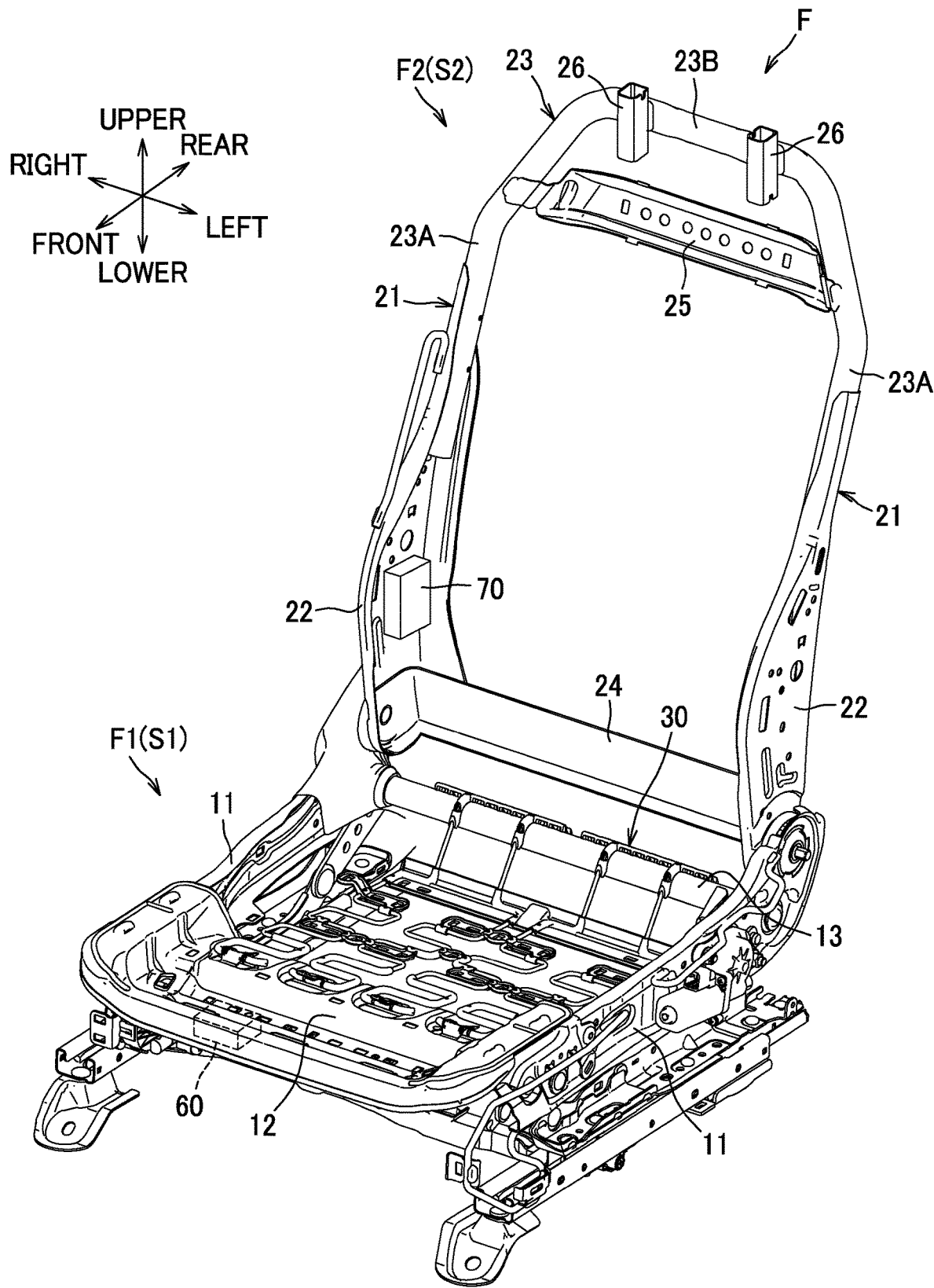
FIG. 11 is a perspective view of a seat frame incorporated in the seat.

The seat body S0 includes a seat cushion S1, a seat back S2, and a headrest S3. The seat body S0 comprises a seat frame F as shown in FIG. 11, and is configured such that the seat frame F is upholstered with a pad made of urethane foam or the like and an outer covering made of fabrics, leather or the like. The seat frame F includes a cushion frame F1 which constitutes a frame of the seat cushion S1, and a back frame F2 which constitutes a frame of the seat back S2.

Figure 12:
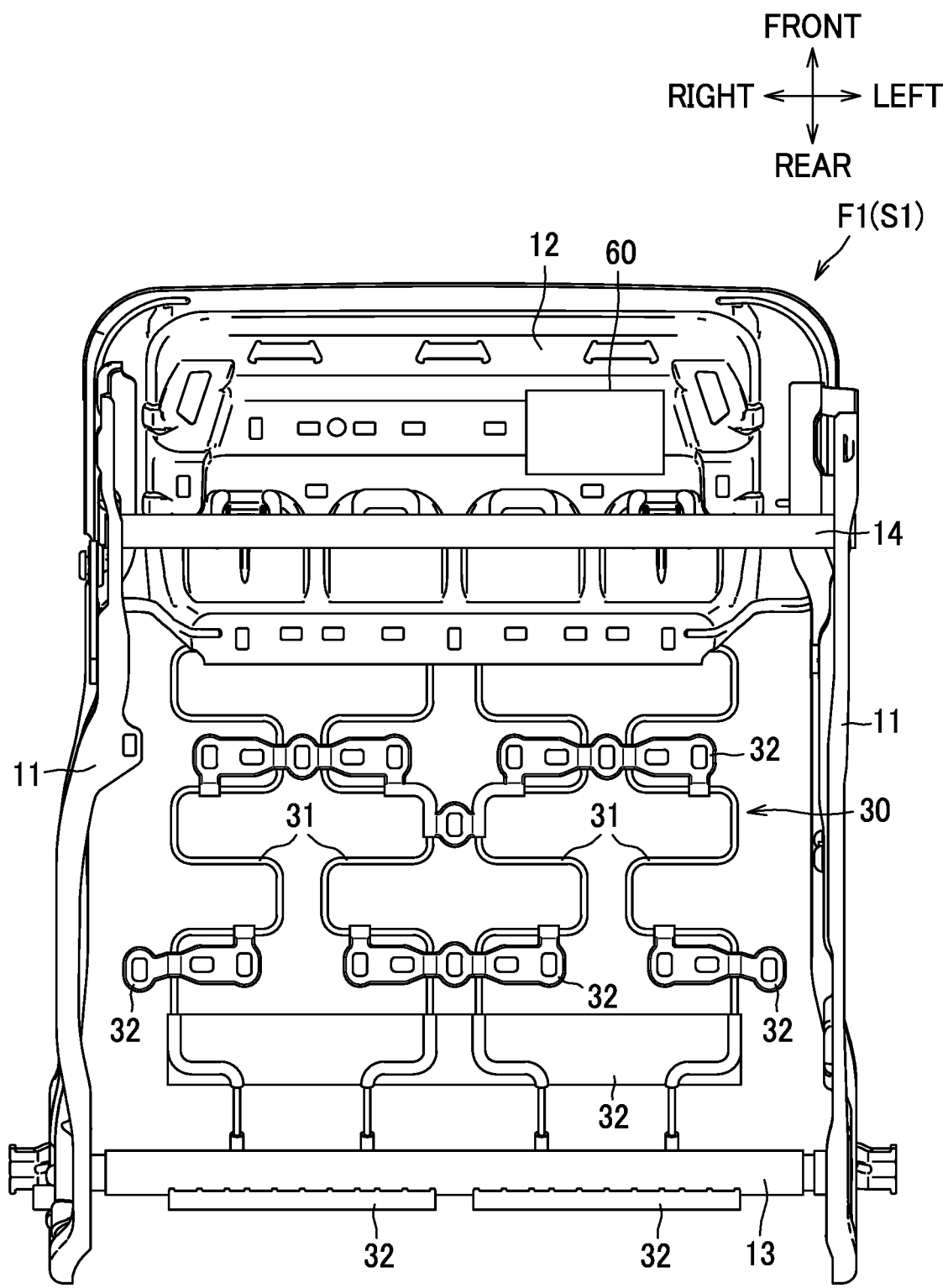
FIG. 12 is a bottom view of a cushion frame that makes up the seat frame, as viewed from below.

The cushion frame F1 (seat cushion S1) includes a pair of left and right cushion side frames 11, a pan frame 12, a rear frame 13, and a front frame 14 (see FIG. 12).

The pair of cushion side frames 11 are members which constitute left and right frames of the seat cushion S1, and are made of sheet metal.

The pan frame 12 is made of sheet metal, and so provided as to connect front portions of the pair of cushion side frames 11.

As shown in FIG. 12, each of the rear frame 13 and the front frame 14 is made of a pipe. The rear frame 13 connects rear portions of the pair of cushion side frames 11, and the front frame 14 is disposed under the pan frame 12 and connects the front portions of the pair of cushion side frames 11.

Provided between the pair of cushion side frames 11 is a support member 30 which receives a load from an occupant seated on the seat body S0. The support member 30 comprises a plurality of wire members 31 extending generally in a front-rear direction while meandering with alternate turns to the left and to the right, and a plurality of plastic members 32 joining the wire members 31. The support member 30 is stretched between the pan frame 12 and the rear frame 13.

As shown in FIG. 11, the back frame F2 (seat back S2) includes a pair of left and right sheet metal frames 22, a pipe frame 23, a lower frame 24, and a bridging frame 25.

The pair of sheet metal frames 22 are made of sheet metal, and located left and right apart from each other.

The pipe frame 23 is made of piping, and includes a pair of upper side frames 23A, and an upper frame 23B connecting upper ends of the pair of upper side frames 23A. The pair of upper side frames 23A have their lower portions connected to the upper portions of the sheet metal frames 22, so that the pair of upper side frames 23A and the pair of sheet metal frames 22 combined together form a pair of back side frames 21 that constitute left and right frames of the seat back S2. Fixed on the upper frame 23B are a pair of brackets 26 located left and right apart from each other. A pair of pillars S31 of the headrest S3 is attached to the brackets 26 (see FIG. 10).

Each of the lower frame 24 and the bridging frame 25 is made of sheet metal. The lower frame 24 connects lower portions of the pair of back side frames 21, and the bridging frame 25 is located below the upper frame 23B, and connects upper portions of the pair of back side frames 21. The lower frame 24, the bridging frame 25 and the upper frame 23B are an example of a connecting frame connecting a pair of back side frames 21.

As shown in FIG. 10, the pressure sensors PS1 to PS6 are sensors configured to acquire measurement values for use in detecting a state of an occupant seated on the seat body S0. To be more specific, the pressure sensors PS1 to PS6 acquire values of pressure from an occupant seated on the seat body S0. The pressure sensors PS1 to PS6 are provided in the seat body S0. To be more specific, the pressure sensors PS1 to PS3 are provided under an outer covering of the seat cushion S1, and the pressure sensors PS4 to PS6 are provided under an outer covering of the seat back S2. The respective pressure sensors PS1 to PS6 are provided in pairs, each located left and right, symmetric with respect to a laterally central position of the seat body S0.

The pressure sensors PS1, PS2 are located in positions corresponding to the buttocks of an occupant in the seat cushion S1. To be more specific, the pressure sensors PS1 are provided in positions which correspond to the lowermost portions of ischial bones of the occupant and on which the load of the occupant is borne largest; the pressure sensors PS2 are located a little frontward of the pressure sensors PS1. The pressure sensors PS1, PS2 are configured to acquire values of pressure from the buttocks of the occupant.

The pressure sensors PS3 are located frontward of and distanced far from the pressure sensors PS1 and the pressure sensors PS2, specifically, in positions corresponding to the thighs of the occupant. The pressure sensors PS3 are configured to acquire values of pressure from the thighs of the occupant.

The pressure sensors PS4, PS5 are located in a lower portion of the seat back S2. To be more specific, the pressure sensors PS4 are located in positions corresponding to the back of the lumbar region of the occupant; the pressure sensors PS5 are located in positions a little higher than the positions of the pressure sensors PS4. The pressure sensors PS4, PS5 are configured to acquire values of pressure from the lumbar region of the occupant.

The pressure sensors PS6 are located above and distanced far from the pressure sensors PS4, PS5, specifically, in positions corresponding to an upper part of the back of the occupant. The pressure sensors PS6 are configured to acquire values of pressure from the region corresponding to the scapulae of the back of the occupant.

The communication unit 60 is a device capable of communicating with a server 90 as an example of a device outside the seat body S0 via a network N such as the Internet. As shown in FIG. 12, in the present embodiment, the communication unit 60 is provided in the seat cushion S1. To be more specific, the communication unit 60 is located under the pan frame 12, and attached to the pan frame 12.

Figure 13:
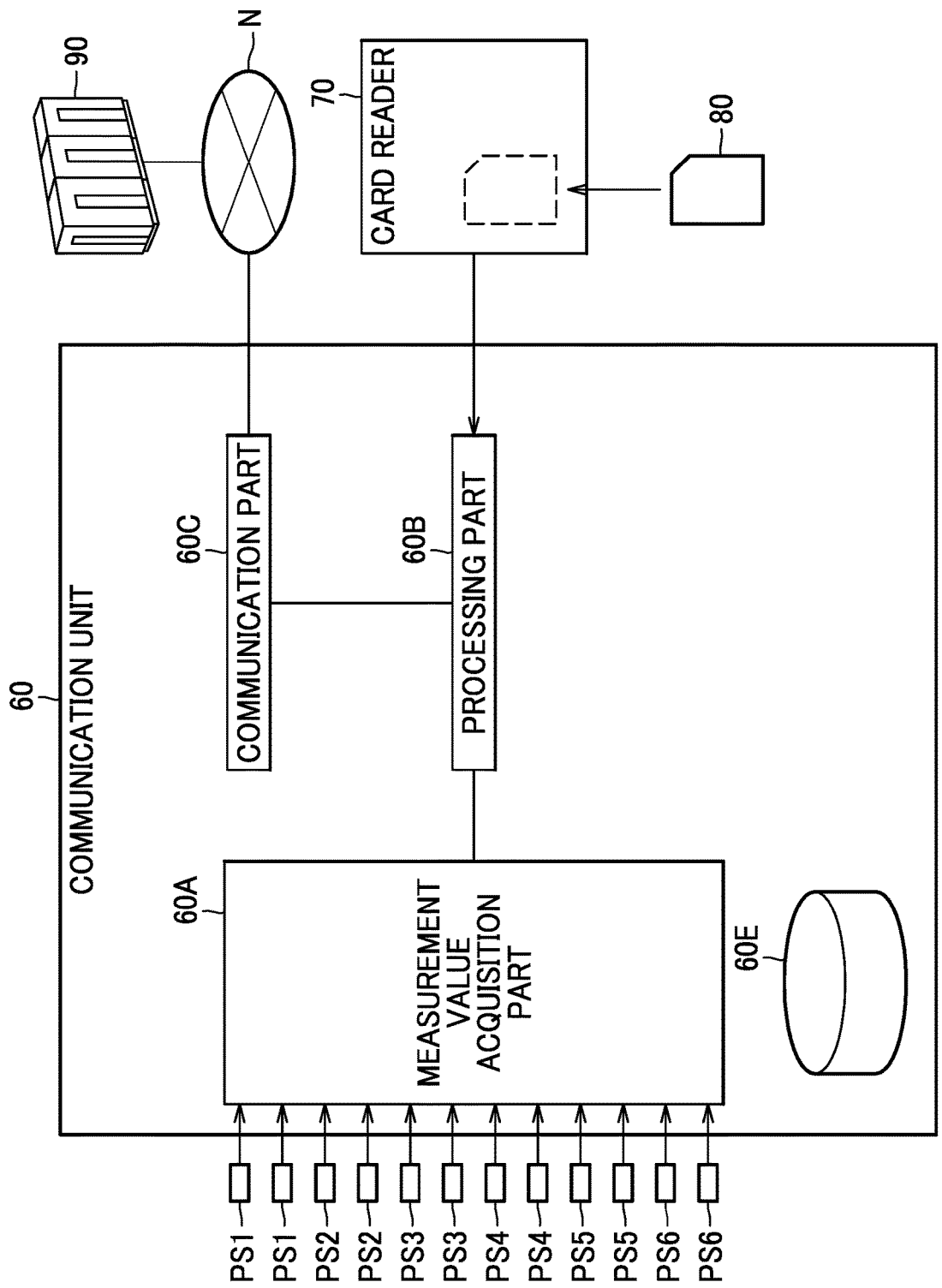
FIG. 13 is a block diagram showing a configuration of the seat.
Figure 15:
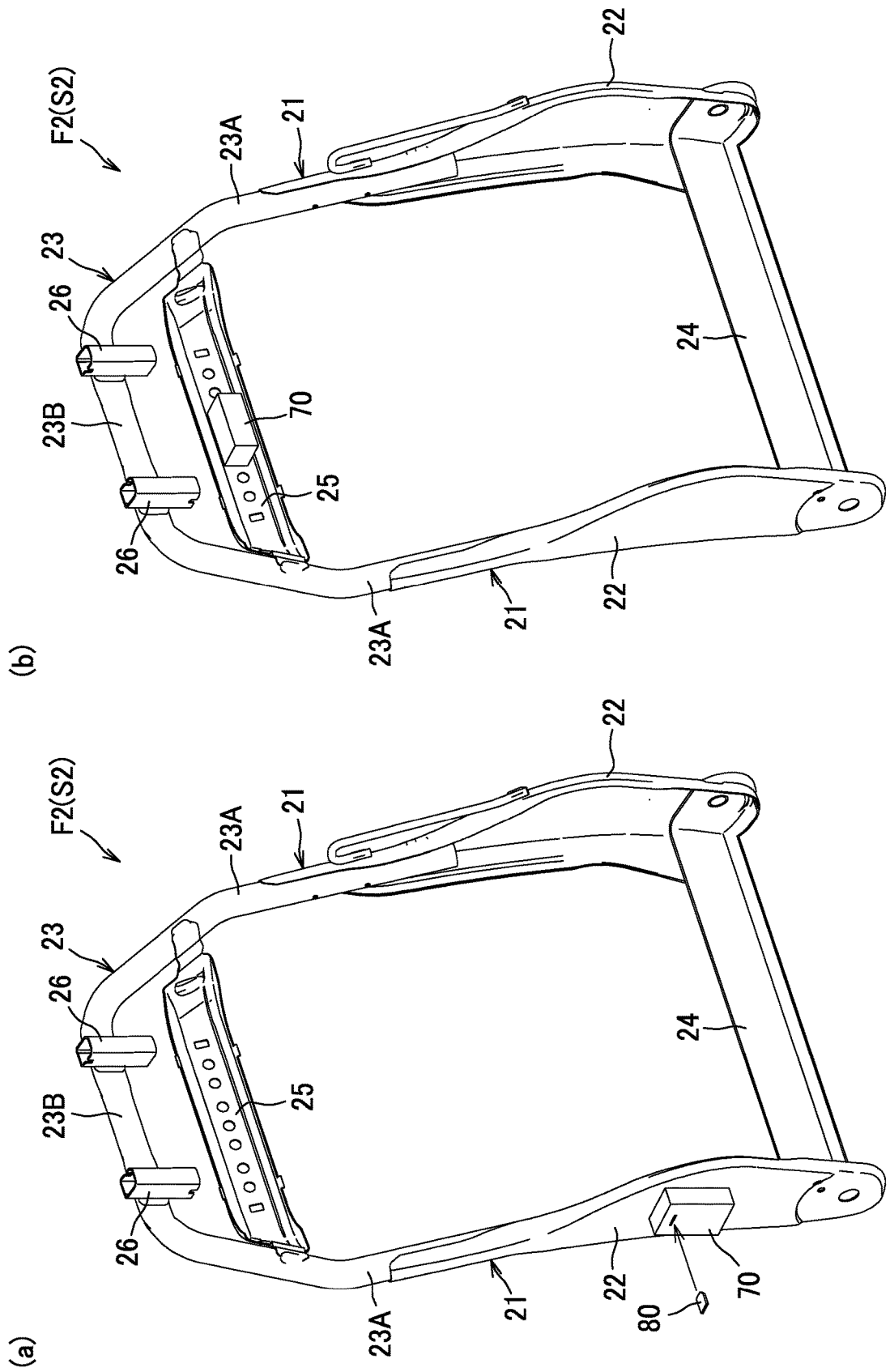
FIG. 15 includes perspective views showing a back frame and a card reader of a seat as modified examples, including (a) a first modified example and (b) a second modified example.

As shown in FIG. 13, the communication unit 60 mainly includes a measurement value acquisition part 60A, a processing part 60B, a communication part 60C, and a storage part 60E.

The measurement value acquisition part 60A has a function of acquiring pressure values as measurement values from the respective pressure sensors PS1 to PS6. To this end, the measurement value acquisition part 60A is connected to, and thus made capable of acquiring pressure values from, the respective pressure sensors PS1 to PS6. The pressure values acquired by the measurement value acquisition part 60A are stored in the storage part 60E, and used in the processing part 60B. The storage part 60E is used to store data required for processing, etc. in the communication unit 60C, on an as-appropriate basis.

The processing part 60B has a function of executing processes of converting pressure values acquired from the respective pressure sensors PS1 to PS6 into data in a format suitable for transmission to the server 90, and of enabling the communication part 60C to establish communication, and the like.

The communication part 60C has a function of radio communication with the server 90 via the network N. The communication part 60C is capable of transmitting to the server 90 information based on pressure values. Such information based on pressure values may be the pressure values themselves acquired from the pressure sensors PS1 to PS6, or may not be the pressure values themselves but may be other information such as information related to motion of an occupant, for example, as identified by the processing part 60B based on the pressure values.

The card reader 70 is a device which a SIM (subscriber identity module) card 290 as an example of a recording medium is insertable in and ejectable from, and which is capable of reading identification information (which will be described later) recorded in the SIM card 80 when the SIM card 80 is inserted therein. The SIM card 80 as a recording medium is an IC (integrated circuit) card in which identification information such as an ID number for use in identifying a seat S10 is recorded. There are no particular limitations on the size of the SIM card 80. In this specification, "SIM card" is referred to as a term including any IC cards having similar functions, such as, for example, UIM (user identity module) cards, USIM (universal SIM) cards, R-UIM (removable UIM) cards, etc.

The card reader 70 is connected to the communication unit 60 via a wire. The card reader 70 is capable of transmitting to the processing part 60B of the communication unit 60 identification information read out from the SIM card 80. The processing part 60B executes the process of enabling the communication part 60C of the communication unit 60 to establish radio communication with the server 90 based on the identification information read out by the card reader 70.

As shown in FIG. 10, the card reader 70 is provided in the seat body S0. In this embodiment, the card reader 70 is provided in the seat back S2 selected among several portions of the seat body S0. Specifically, as shown in FIG. 11, the card reader 70 is attached to one of the pair of back side frames 21 selected among several portions of the seat frame F.

To be more specific, the card reader 70 is located between the pair of back side frames 21 arranged side by side in the lateral direction of the seat body S0. The card reader 70 is attached to a laterally inner side of one of the left and right back side frames 21 (in this embodiment, right back side frame 21) of the seat body S0.

As shown in FIG. 14(a), the right back side frame 21 which makes up the seat frame F (specifically, the right sheet metal frame 22) has a first slot hole 21A in a position corresponding to a card insertion slot (not shown) of the card reader 70. The first slot hole 21A is a hole which permits the SIM card 80 to pass therethrough to be inserted in and ejected from the card reader 70. In the present embodiment, the first slot hole 21A is configured as an elongate hole with its longitudinal direction oriented parallel to the front-rear direction.

As shown in FIG. 14(b), the seat body S0 includes a first panel 41 as a panel exposed on outside while covering at least part of the seat frame F, and a first cover 42 as a cover. In this embodiment, the first panel 41 and the first cover 42 are made of plastic. The first panel 41 is attached to the right back side frame 21 and so provided as to cover part of a laterally outer side (right side) surface of the right back side frame 21 of the seat body S0. Specifically, the part of the side surface of the right back side frame 21 which the first panel 41 covers is a part in which the first slot hole 21A is formed.

The first panel 41 has a card insertion region 41A in a recessed shape with a bottom region 41B, and a second slot hole 41C formed in the bottom region 41B of the card insertion region 41A. The second slot hole 41C is provided, in a position corresponding to the first slot hole 21A of the back side frame 21, to communicate with the first slot hole 21A. The second slot hole 41C is a hole which permits the SIM card 80 to pass therethrough to be inserted in and ejected from the card reader 70, and is formed, in the present embodiment, as an elongate hole with its longitudinal direction oriented parallel to the front-rear direction, similar to the first slot hole 21A.

The first cover 42 is configured to be capable of being shifted in position to a state in which the second slot hole 41C is covered therewith and to a state in which the second slot hole 41C is uncovered. Specifically, the first cover 42 is attachable to and detachable from the card insertion region 41A of the first panel 41, so that when attached to the first panel 41 as indicated by a chain double dashed line, it covers the second slot hole 41C, and when detached from the first panel 41 as indicated by a solid line, it uncovers the second slot hole 41C.

According to the present embodiment described above, the seat S10 includes the communication unit 60 and the card reader 70 capable of reading out identification information recorded in the SIM card 80; therefore, the seat S10 can be individually identified by means of the identification information recorded in the SIM card 80, and allowed to establish radio communication with the server 90.

Moreover, by the communication unit 60, information based on measurement values (pressure values) of the pressure sensors PS1 to PS6 provided in the seat body S0 can be transmitted to the server 90 provided outside the seat body S0. Accordingly, versatility of information based on the pressure values from the pressure sensors PS1 to PS6 provided in the seat body S0 can be increased. For example, the pressure values transmitted from a plurality of seats S10 may be accumulated in the server 90, and a posture of an occupant, or the like may be analyzed based on the accumulated pressure value information, so that information can be utilized for development of such seats as more comfortable, less prone to feeling fatigued even after extended use, etc. Furthermore, for example, when a system for identifying a motion of an occupant from pressure value information is to be constructed, accumulated pressure value information may be utilized for analysis so that precision of the motion identification can be improved.

Since the card reader 70 is attached to the seat frame F that is a frame of the seat body S0, the card reader 70 can be provided in the seat body S0 in a stable state. To elaborate, since the card reader 70 is attached to the back side frame 21 that makes up the seat frame F, the card reader 70 can be provided in a stable manner in the seat back S2.

Since the back side frame 21 that makes up the seat frame F has the first slot hole 21A, a SIM card 80 is allowed to pass through the first slot hole 21A so that the SIM card 80 can be inserted in and ejected from the card reader 70. Moreover, with this configuration, the card reader 70 can be located on a laterally inner side (right or left side) of the left or right back side frame 21 of the seat body S0; therefore, the card reader 70 can be protected by the back side frame 21 that makes up the seat frame F.

Since the first panel 41 with which part of the back side frame 21 is covered has the second slot hole 41C, a SIM card 80 can be inserted in and ejected from the card reader 70 through the second slot hole 41C. Moreover, the card reader 70 and a SIM card 80 inserted in the card reader 70 can be protected by the first panel 41 and the first cover 42.

To the second embodiment described above, modifications of specific configurations may be made where deemed appropriate. In the following description, the same elements as of the above-described embodiment will be designated by the same reference characters, and a description will be omitted where appropriate.

In the second embodiment, the card reader 70 is attached to a laterally inner side (right or left side) of one of the left and right back side frames 21 of the seat body S0; however, for example, as shown in FIG. 15(a), the card reader 70 may be attached to an outer side of one of the back side frames 21.

Alternatively, as shown in FIG. 15(b), the card reader 70 may be attached to a front side of the bridging frame 25 as an example of a connecting frame. With this alternative configuration in which the card reader 70 is attached to the bridging frame 25 (connecting frame) as well, the card reader 70 can be provided in a stable state in the seat back S2. It is to be understood that the configuration shown in FIG. 15(b) may be modified, so that the configuration in which the bridging frame 25 has a first slot hole formed therein may be adopted (see FIG. 14(a)), and the configuration in which the bridging frame 25 is covered with a first panel and/or a first cover may be adopted (see FIG. 14(b)). The card reader 70 may be attached to a rear side of the bridging frame 25.

As shown in FIG. 16(a), the card reader 70 may be attached to a front side of the upper frame 23B. The card reader 70 is located between the pair of brackets 26 arranged side by side in the lateral direction of the main body S0. With this configuration, the card reader 70 can be located in an upper part of the seat back S2 to which the headrest S3 is attached, so that a SIM card 80 can be inserted in and ejected from the card reader 70 with ease.

Another configuration as shown in FIG. 16 (b) may be feasible, in which the seat body S0 includes a second panel 51 as a panel exposed on outside between the pair of brackets 26, and a second cover 52 as a cover. The second panel 51 and the second cover 52 are made of plastic. The second panel 51 is attached to the back frame F2, and so located as to cover an upper side of the card reader 70.

The second panel 51 has a card insertion region 51A in a recessed shape with a bottom region 51B, and a second slot hole 51C formed in the bottom region 51B of the card insertion region 51A. The second slot hole 51C is provided in a position corresponding to a card insertion slot (not shown) of the card reader 70. The second slot hole 51C is a hole which permits a SIM card 80 to pass therethrough to be inserted in and ejected from the card reader 70, and in this embodiment, is configured as an elongate hole with its longitudinal direction oriented parallel to the lateral direction.

The second cover 52 is configured to be capable of being shifted in position to a state in which the second slot hole 51C is covered therewith and to a state in which the second slot hole 51C is uncovered. Specifically, the second cover 52 is attachable to and detachable from the card insertion region 51A of the second panel 51, so that when attached to the second panel 51 as indicated by a chain double dashed line, it covers the second slot hole 51C, and when detached from the second panel 51, as indicated by a solid line, it uncovers the second slot hole 51C.

With this configuration, a SIM card 80 can be inserted in and ejected from the card reader 70 through the second slot hole 51C. Moreover, the card reader 70 and a SIM card 80 inserted in the card reader 70 can be protected by the second panel 51 and the second cover 52.

It is to be understood that the second cover 52 may also be so provided as to be slidable or rotatable relative to the second panel 51, and configured to be thereby rendered openable and closeable relative to the second panel. The same goes for the first cover 42 mentioned above.

The card reader 70 may be attached to a rear side of the upper frame 23B. The card reader 70 may be attached to a front or rear side of the lower frame 24 (see FIG. 15).

Although the card reader 70 (information reading part) in the second embodiment is provided in the seat back S2, it may be provided, for example, in the seat cushion S1 of the seat body S0. For example, as shown in FIGS. 17(a), (b), an information reading part 60D which permits a SIM card 80 to be inserted in and ejected from may be attached to a pan frame 12 of the seat cushion S1. With this configuration in which the information reading part 60D is attached to the pan frame 12, the information reading part 60D can be provided in the seat cushion S1 in a stable state. In this embodiment, the information reading part 60D is formed integrally with a communication unit 60 in one piece, and the communication unit 60 has a card insertion slot 61 at its front side.

As shown in FIG. 18(a), a card reader 70 as an information reading part may be attached to one of the pair of cushion side frames 11. In this embodiment, the card reader 70 is attached to a laterally outer side (left or right side) of one of the left and right cushion side frames 11 of the seat body S0. In this arrangement of the card reader 70 attached to the cushion side frame 11, as well, the card reader 70 can be provided in the seat cushion S1 in a stable state.

Alternatively, as shown in FIG. 18(b), the card insertion slot 71 of the card reader 70 may be collocated with switches 15A, 15B for operating a front-rear position adjustment mechanism, height adjustment mechanism, reclining mechanism, etc. of the seat. Such arrangement may also be similarly applied to the configuration in which the card reader 70 is attached to the back side frame 21 of the seat back S2.

Where the card reader 70 is provided in the seat cushion S1, the card reader 70 may be attached to a laterally inner side (right or left side) of one of the left and right cushion side frames 11 of the seat body S0. In this configuration, the first slot hole may be provided in the cushion side frame 11 to which the card reader 70 is attached (see FIG. 14(a)), and further, this cushion side frame 11 may be covered with the first panel and/or the first cover (see FIG. 14(b)).

In the embodiments described above, the card reader 70 is attached to the seat frame F, such as the side frames 11, 21, the pan frame 12, the connecting frame (23B, 24, 25), etc.; however, the card reader 70 may not be attached to the seat frame F, but may be attached to the support member 30, or S spring provided in place of the support member 30.

In the embodiments described above, the card reader 70 is provided in the seat cushion S1 or the seat back S2; however, the card reader 70 may be provided, for example, in the headrest S3. Alternatively, the card reader 70 may be provided in an armrest or an ottoman (not shown).

Figure 19:
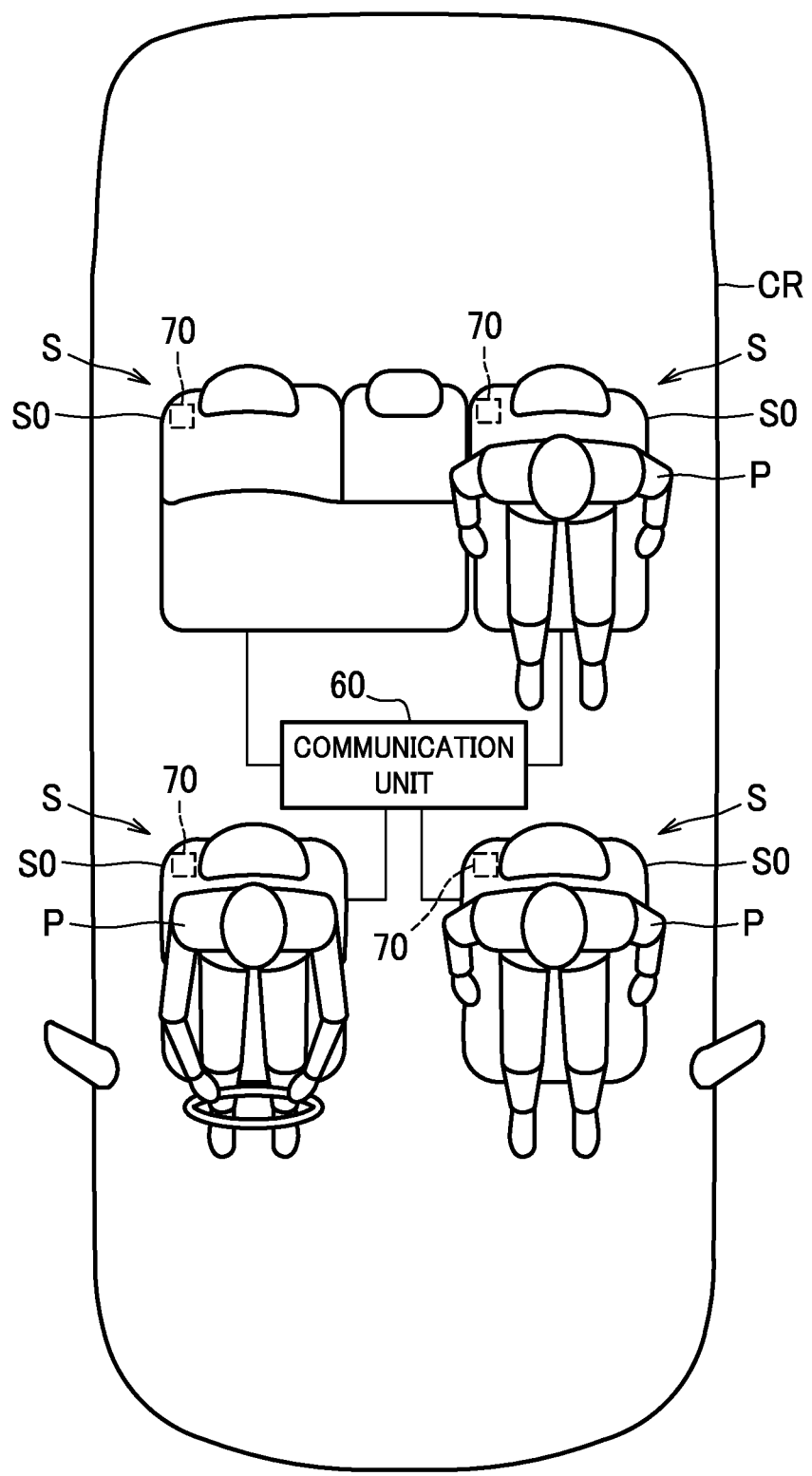
FIG. 19 is a diagram showing a car in which a sixth modified example of a seat is installed.

In the embodiments described above, the communication unit 60 (radio communication part) is provided in the seat body S0; however, the communication unit 60 may be provided outside the seat body S0. For example, as shown in FIG. 19, where four seat bodies S0 for occupants P to be seated thereon, including two front seats and two rear seats, are provided in the car CR, the communication unit 60 may be shared among the four seat bodies S0, and located outside each seat body S. In such configurations as with a plurality of seat bodies S0 provided in the car CR, the card reader 70 may be provided for each of the seat bodies S0 (see FIG. 19), or may be provided for only one of the seat bodies S0 (i.e., only one card reader may be provided in the car CR). Where the card reader 70 is provided for each of the seat bodies S0, identification information for use in individually identifying each seat body S0 is recorded in the SIM card.

Although the recording medium illustrated in the second embodiment is the SIM card 80, the recording medium may be an IC card other than the SIM card, as long as identification information enabling radio communication by the radio communication part is recorded; furthermore, any recording medium other than the IC card may also be applicable. When a recording medium other than the IC card is adopted, needless to say, the information reading part is configured to be compatible with the adopted recording medium.

Although the pressure sensors PS1 to PS6 are illustrated as an example of sensors in the second embodiment, the sensor may be a sensor other than a pressure sensor, for example, a temperature sensor, a humidity sensor, an acoustic sensor, an photo sensor, a heart rate sensor, a respiratory sensor, an occupant motion detecting sensor, an occupant sweat detecting sensor, etc. The sensors provided in the seat body may not be of a single kind, but may be of a plurality of kinds.

Although the server 90 is illustrated as an example of a device outside the seat body S0 in the second embodiment, such a device may be any computer other than a server.

Although the seat S10 installed in an automobile is illustrated as an example of a seat in the second embodiment, the seat may be a seat installed in a vehicle other than an automobile, such as a railcar, a ship or aircraft. The seat may not be limited to a vehicle seat, but may be a seat for home use, or a seat installed in facilities.

Any of the elements explained in relation to the exemplified embodiments and illustrative modified examples disclosed in this description may be implemented in combination as desired.

The invention claimed is:

1. An in-seat experience system comprising:
 a seat, comprising:
  a seat body installed in a car,
  a sensor provided in the seat body, the sensor configured to acquire a measurement value for use in identifying motion of an occupant seated on the seat body, and
  a seat controller connected to the sensor, the seat controller configured to acquire the measurement value from the sensor;
 a global positioning system (GPS) receiver configured to acquire location information of the seat;
 an experience instruction device connected to the seat controller, the experience instruction device having installed therein an experience application that is configured to notify an occupant seated on the seat body of a motion instruction and to provide an experience to the occupant,
  wherein the experience instruction device is configured to store user identification information for use in identifying the occupant; and
 a server configured to communicate with the experience instruction device,
  wherein the experience instruction device is further configured to:
   determine, based upon a measurement value from the sensor, as to whether or not a first condition is satisfied, after the experience provided by the experience application ends, and
   transmit a result of the determination to the server when the first condition is satisfied,
  wherein in response to a determination being made that the first condition is satisfied, the server or the experience instruction device acquires the location information of the seat from the GPS receiver, and the server or the experience instruction device determines that a second condition is satisfied if a distance traveled from a most recent location of the seat to a present location of the seat is equal to or greater than a threshold value, the most recent location being a location of the seat acquired a most recent time that a point score had increased,
  wherein the server increases the point score stored for the corresponding user identification information if the first condition and the second condition are satisfied, and does not increase the point score if the first condition is satisfied but the second condition is not satisfied, and
  wherein the server or the experience instruction device resets the most recent location by setting the current location as the most recent location after the server increases the point score.

2. The in-seat experience system according to claim 1, wherein the seat body comprises an outer covering, and wherein the sensor is a pressure sensor provided under the outer covering.

3. The in-seat experience system according to claim 1, wherein the server stores fellowship of the occupant and a fellow user as association data indicating correlations between user identification information of the occupant and user identification information of the fellow user, and
 wherein the server or the experience instruction device is further configured to:
  determine, if the first condition and the second condition are satisfied, whether or not a third condition is satisfied as to whether an in-seat experience is enjoyed simultaneously by the occupant and the fellow user, and
  increase the point score if the third condition is satisfied.

4. The in-seat experience system according to claim 1, wherein the server stores fellowship of the occupant and a fellow user as association data indicating correlations between user identification information of the occupant and user identification information of the fellow user, and
 wherein the server or the experience instruction device is further configured to:
  determine, when the first condition and the second condition are determined to be satisfied, whether or not a third condition that an in-seat experience being enjoyed simultaneously by the occupant and the fellow user is satisfied, and
  increase the point score, if the third condition is satisfied, by a number of points greater than a number of points increased when the third condition is not satisfied.

5. The in-seat experience system according to claim 1, wherein the seat body comprises a seat cushion, a seat back, and a headrest, the seat body being formed by upholstering a seat frame with a pad and an outer covering,
 wherein the seat frame comprises a cushion frame that constitutes a frame of the seat cushion, and a back frame that constitutes a frame of the seat back,
 wherein the cushion frame comprises a pair of left and right cushion side frames, a pan frame, a rear frame, and a front frame, and
 wherein a support member is provided between the pair of left and right cushion side frames and is configured to receive a load from the occupant seated on the seat body.

6. A method for manufacturing an in-seat experience system, the method comprising:
 providing a seat comprising:
  a seat body installed in a car,
  a sensor provided in the seat body, the sensor configured to acquire a measurement value for use in identifying motion of an occupant seated on the seat body, and
  a seat controller connected to the sensor, the seat controller configured to acquire the measurement value from the sensor;
 providing a global positioning system (GPS) receiver configured to acquire location information of the seat;
 providing an experience instruction device connected to the seat controller, the experience instruction device having installed therein an experience application that is configured to notify an occupant seated on the seat body of a motion instruction and to provide an experience to the occupant, wherein the experience instruction device is configured to:

store user identification information for use in identifying the occupant;

providing a server configured to communicate with the experience instruction device;

determine, based upon a measurement value from the sensor, as to whether or not a first condition is satisfied, after the experience provided by the experience application ends, and transmit a result of the determination to the server when the first condition is satisfied;

providing a server configured to communicate with the experience instruction device;

configuring the server or the experience instruction device to:

in response to a determination that the first condition is satisfied, acquire the location information of the seat from the GPS receiver, and determine that a second condition is satisfied if a distance traveled from a most recent location of the seat to a present location of the seat is equal to or longer than a threshold value, the most recent location being a location of the seat acquired a most recent time that a point score had increased;

configuring the server to:

increase a point score stored for the corresponding user identification information if the first condition and the second condition are satisfied, and not increase the point score if the first condition is satisfied but the second condition is not satisfied; and further configuring the server or the experience instruction device to reset the most recent location by setting the current location as the most recent location after the server increases the point score.

\* \* \* \* \*